(12) United States Patent
Higo et al.

(10) Patent No.: US 6,330,471 B1
(45) Date of Patent: Dec. 11, 2001

(54) IONTOPHORESIS ELECTRODE DEVICE

(75) Inventors: Naruhito Higo; Tatsuya Meno, both of Ibaragi-ken (JP)

(73) Assignee: Hisamitsu Pharmaceutical Co., Ltd., Saga-ken (JP)

( * ) Notice: Subject to any disclaimer, the term of this patent is extended or adjusted under 35 U.S.C. 154(b) by 0 days.

(21) Appl. No.: 09/142,758

(22) PCT Filed: Jan. 20, 1997

(86) PCT No.: PCT/JP97/00113

§ 371 Date: Feb. 10, 1999

§ 102(e) Date: Feb. 10, 1999

(87) PCT Pub. No.: WO97/34657

PCT Pub. Date: Sep. 25, 1997

(30) Foreign Application Priority Data

Mar. 17, 1996 (JP) .................................................. 8-088736

(51) Int. Cl.[7] .................................................. A61N 1/30
(52) U.S. Cl. .................................................. 604/20
(58) Field of Search .............................. 604/20; 607/149, 607/153; 424/4.49

(56) References Cited

U.S. PATENT DOCUMENTS

| 4,722,726 | * | 2/1988 | Sanderson et al. | 604/20 |
| 4,764,164 | * | 8/1988 | Sasaki | 604/20 |
| 5,125,894 | * | 6/1992 | Phipps et al. | 604/20 |
| 5,395,310 | * | 3/1995 | Untereker et al. | 604/20 |
| 5,405,317 | * | 4/1995 | Myers et al. | 604/20 |
| 5,543,098 | * | 8/1996 | Myers et al. | 264/104 |
| 5,607,691 | * | 3/1997 | Hale et al. | 424/449 |

FOREIGN PATENT DOCUMENTS

| 2129242 | 8/1993 | (CA) | A61N/1/30 |
| 61-149168 | 7/1986 | (JP) | A61N/1/30 |
| 63-35266 | 2/1988 | (JP) | A61N/1/30 |
| 63-502404 | 9/1988 | (JP) | A61N/1/30 |
| 3-51062 | 3/1991 | (JP) | A61N/1/30 |

* cited by examiner

Primary Examiner—Richard K. Seidel
Assistant Examiner—Michael Hayes
(74) Attorney, Agent, or Firm—Sughrue, Mion, Zinn, Macpeak & Seas, PLLC

(57) ABSTRACT

The object of the present invention is to provide an iontophoresis electrode device with superior performance which avoids entrance of metal ions from the electrode into the body, is reusable and can be mass produced at low cost, minimizes gas generation which causes polarization, can notably improve transport current, and can prevent skin injury by pH changes during prolonged application.

The iontophoresis electrode device of the present invention has a construction provided with a backing 1 having an edge section 1a around an opening and a packing chamber 4 inside, an electrode terminal 2 situated in the packing chamber 4, a non-adhesive gel 5 containing an electrolyte solvent, depolarizer, pH regulator and drug packed in the packing chamber 4, an inert electrode member 3 covering the base of the electrode terminal 2, and a liner 7 attached to the adhesive layer 6 coated on the edge section 1a and covering the opening.

31 Claims, 6 Drawing Sheets

IONTOPHORESIS ELECTRODE DEVICE

TECHNICAL FIELD

The present invention relates to an iontophoresis electrode device which is suitable for transdermal or transmucosal therapy. More specifically, it relates to an iontophoresis electrode device used for transdermal and transmucosal drug administration based on the principle of iontophoresis, which iontophoresis electrode device results in no penetration of harmful metal ions into the body from the reactive electrodes and no pH change-related skin damage, produces no voltage increase or current reduction by polarization, and can be mass produced at low cost.

BACKGROUND ART

Many types of dosage forms have been developed in recent years in the field of external applications, and they have continued to attract a great deal of interest. This is because of a number of advantages, including the fact that local or systemic administration of a drug with an expected pharmacological effect through skin or a mucous membrane can provide a sustained drug effect, that adjustment of the absorption rate of the drug is easier so that side effects of overdoses can be prevented, that there is less of an effect of metabolism by initial passage through the liver as occurs with oral administration, and that administration can therefore be rendered relatively safer with drugs associated with liver damage, etc.

However, because normal skin has a protective function against stimulants from the outside, absorption and passage of drugs is comparatively more difficult. Consequently, it is presently the case that when drugs in external preparation form are administered their absorption is poorer and therefore their desired drug effects are more difficult to obtain.

Even by using absorption routes through biological membranes other than the skin, such as oral, rectal, buccal, nasal, sublingual, etc., there are still a great number of drugs which do not easily penetrate or pass through those biological membranes, and thus have low bioavailability.

Consequently, there is a demand for a highly useful and safe method for accelerating drug absorption, which sufficiently increases penetration, passage and absorption through the skin and other biological membranes to allow drug effects to be adequately exhibited at practically useful doses, and which itself results in minimal local toxicity or systemic toxicity.

Current absorption accelerating methods include accelerating methods employing absorbefacients and accelerating methods employing iontophoresis or phonophoresis. In particular, iontophoresis has rapidly attracted attention in recent years, and offers promise as a method of administration which can overcome the aforementioned problems.

Iontophoresis is a method of administering a drug through skin or a mucous membrane whereby a voltage is applied to the skin or mucous membrane to induce electrical migration of ionic drugs.

Iontophoresis electrode devices generally have a construction geared for therapy, whereby anode and cathode iontophoresis electrode devices are attached to the skin at a prescribed spacing, and the current generated from a current generator is fed to the electrode devices.

The electrode devices are constructed with the electrodes in combination with a layer which stores the drug or conducting medium, including a pre-designed fixed dose of the drug component together with various additives if necessary for stable maintenance of the drug effect, in order to administer a continuous controlled dose of the drug component to the body environment during a prescribed period.

When a current is applied to a membrane (such as skin) with polarization impedance, which has a low electrode reaction rate upon application of the current pulse or a low concentration of substances contributing to the electrode reaction, a polarization current is discharged upon termination of the pulse. Since the polarization current is a current flowing in the opposite direction from the current flowing by application of the pulse current, the net flow of current is the applied current minus the polarization current. This is the current responsible for penetration of the drug, and it is therefore defined as the transport current. A small transport current indicates poor efficiency in terms of drug penetration. Much research has been conducted with the purpose of solving these problems.

For example, in Japanese Laid-open Patent Publication No. 149168 of 1986 (hereunder referred to as Publication A) there is disclosed "an iontophoresis electrode device with an improved electrode, comprising a drug source to be supplied by ion introduction, means for carrying the drug source, and at least one electrochemically active component which is electrically connected with the drug source and undergoes a slight degree of hydrolysis during the ion introduction period", whereby the drug to be supplied by ion introduction, the electrochemically active component of the device, or both, are deliberately selected so as to reduce formation of undesirable hydrolysates during operation of the device.

In Japanese Laid-open Patent Publication No. 35266 of 1988 (hereunder referred to as Publication B) there is disclosed "an iontophoresis electrode device provided with a first electrode, a second electrode, means by which the first electrode communicates with a drug solution, means by which the drug solution communicates with a patient while said drug solution is situated between the first electrode and the patient, means by which the second electrode communicates with the patient at a distal point from the first electrode in the patient, and means by which a potential difference is created between the first electrode and second electrode in such a manner that the potential difference passes through the skin of the patient for transport of the drug ions, and by which an insoluble deposit is produced by reaction of the first electrode with the complementary ion, thus removing from the drug medium the ion which competes with the drug ion for charge transport and reduces the amount of drug administered to the patient", whereby the pH of the drug medium is controlled without a buffering agent to minimize production of the competing ion and thus maintain a dose of the administered drug in proportion to the current.

In Japanese Laid-open Patent Publication No. 502404 of 1988 (hereunder referred to as Publication C) there is disclosed "an iontophoresis electrode device provided with a first housing member containing an electrolyte, an electrode for the first housing member which contacts with the electrolyte in the housing member, a second housing member adjacent to the first housing member and designed to contain an effective component, an ion-exchange membrane as an ion migration-inhibiting member separating the first housing member and the second housing member, in order to inhibit the flow between the first and second housing members by ions with a charge equivalent to the effective component which has been at least partially ionized, and a support member for supporting the effective component in the second housing member when it passes through the skin of the patient to allow penetration of the ions of the effective component", the purpose of which is to increase the speed and efficiency of drug transport to the patient, and to reduce the chance of chemical burn injury which occurs by uncontrolled production of protons or hydroxide ions at the electrodes during ion introduction delivery of the drug, or of injury to the skin including electrical burn injury which occurs due to the use of high current.

In Japanese Laid-open Patent Publication No. 51062 of 1991 (hereunder referred to as Publication D) there is disclosed "an iontophoresis electrode device with a substance which reduces gas generation by hydrolysis situated on the surface of an cathode contacting with a drug solution", whereby the energy consumed by hydrolysis is minimized so that most of the electrical energy is utilized as drug delivery energy.

The following problems have become evident, however, with these constructions of conventional iontophoresis electrode devices. Specifically:

Since the devices described in Publications A and B employ electrochemically reactive electrodes, reuse of the electrodes has been difficult despite the low polarization, while the use of silver, etc. results in higher cost, and they have also been found to have problems of safety since metal ions from the electrodes tend to easily enter the body. Because the device described in Publication C employs an ion-exchange membrane, unnecessary entrance of ions into the body can be prevented, but ion-exchange membranes are generally expensive and also involve technical difficulties in their production. There has also been a problem of lower transport current due to polarization. The method of minimizing gas generation of the inert electrode disclosed in Publication D has had a problem in that polarization cannot be completely prevented, making it difficult to achieve satisfactory results.

When a buffering solution is used as the pH regulator to lower skin injury as described in Publication B, a problem has resulted in that the ions with buffering power enter into the body as electrification progresses, making it impossible to accomplish long-term electrification since the buffering power is lowered. Increasing the buffering power results in more competing ions, which is an undesirable problem in terms of drug penetration.

Consequently, there has been a demand for an iontophoresis electrode device which is safe, gives excellent performance, is reusable and can be produced at low cost.

The present invention overcomes these problems of the prior art and satisfies these demands, and its object is to provide an iontophoresis electrode device with superior performance which ①  is highly safe without entrance of metal ions from the electrode into the body, ② is reusable and can be mass produced at low cost, ③ minimizes gas generation which causes polarization, for notably improved transport current, and ④ can prevent skin injury by pH changes during prolonged application.

DISCLOSURE OF THE INVENTION

In order to achieve the objects described above, the present invention is provided with the following construction.

Specifically, it has a construction wherein an electrode which is basically inert during application is layered with an electrolyte solvent containing a depolarizer in contact with the electrode and/or a pH regulator which is poorly soluble in the electrolyte solvent. When the drug with an expected therapeutic effect is cationic it is included in the anode, and when it is anionic it is included in the cathode. Also, there are no particular restrictions on the method of reinforcing the iontophoresis electrode device, i.e. on the backing composition or structure, or on the method of supporting the solvent or depolarizer (gel, reserver, etc.), and the method of supplying the electrolyte solvent is also not restricted. Some concrete constructions are explained below.

The iontophoresis electrode device according to claim 1 has a construction comprising an inert electrode member and a depolarizer which prevents polarization of the inert electrode member.

The iontophoresis electrode device according to claim 2 has the construction of claim 1 wherein a buffering agent is dispersed or dissolved in the gel of the system, or mixed with the electrolyte solvent.

The iontophoresis electrode device according to claim 3 has the construction of claim 1 which is provided with a pH regulator in the system.

The iontophoresis electrode device according to claim 4 has the construction of claim 3 wherein the pH regulator is a chemical agent which is poorly soluble in the electrolyte solvent.

The iontophoresis electrode device according to claim 5 has the construction of claims 1 to 4, which is further provided with a backing having an edge section at the opening and formed into a cup shape with a packing chamber inside, an electrode terminal situated at a hole formed from the backing to the ceiling of the packing chamber, the inert electrode member which covers the base of the electrode terminal of the packing chamber, an adhesive layer formed on the edge section, and a liner which is attached to the adhesive layer and covers the opening.

The iontophoresis electrode device according to claim 6 has the construction of claim 5 which is provided with a non-adhesive gel containing an electrolyte solvent packed in the packing chamber.

The iontophoresis electrode device according to claim 7 has the construction of claim 6 wherein the non-adhesive gel contains the depolarizer or any one type of the pH regulator and drug.

The iontophoresis electrode device according to claim 8 has the construction of claim 6 which is provided with the drug contained in the non-adhesive gel and a holding material which holds the depolarizer and/or the pH regulator.

The iontophoresis electrode device according to claim 9 has the construction of claim 5 which is provided with a powder mixture included in the packing chamber, a cover member covering the opening, the adhesive layer formed on the cover member or across the cover member and the edge section, an injection hole for injection of the electrolyte solvent and the electrolyte solution prepared by dissolving the depolarizer and drug in the electrolyte solvent, which is open from the backing surface to the ceiling side of the packing chamber, the electrolyte solvent and electrolyte solution which are injected into the packing chamber from the injection hole, and a stopper for sealing the injection hole.

The iontophoresis electrode device according to claim 10 has the construction of claim 9 wherein the powder mixture included in the packing chamber contains at least one type of the depolarizer, pH regulator and drug.

The iontophoresis electrode device according to claim 11 has the construction of claim 9 wherein the electrolyte solution injected through the injection hole is prepared by dissolving at least one type of the depolarizer and drug in the electrolyte solvent.

The iontophoresis electrode device according to claim 12 has the construction of claim 9 wherein the powder mixture included in the packing chamber contains at least one type of depolarizer, pH regulator and drug, and the electrolyte solution is prepared by dissolving in the electrolyte solvent at least one type of a depolarizer or drug other than the type in the powder mixture.

The iontophoresis electrode device according to claim 13 has a construction provided with a flat-formed backing, an electrode terminal situated on the hole of the backing, an inert electrode member covering the base of the electrode terminal, an self-adhesive gel layer formed on the inert electrode member and containing an electrolyte solvent, gel base, depolarizer, pH regulator and/or drug dispersed and dissolved therein, and a liner covered by the self-adhesive gel layer.

The iontophoresis electrode device according to claim 14 has the construction of any of claims 1 to 13, wherein the depolarizer is an electrode reactive substance which has electrode reactivity such that it is preferentially oxidized over hydroxide ions and chloride ions at the inert electrode member, and whose reaction product readily dissolves in the electrolyte solvent.

The iontophoresis electrode device according to claim 15 has the construction of any of claims 1 to 13, wherein the depolarizer is an electrode reactive substance which has electrode reactivity such that it is preferentially reduced over hydrogen ions at the inert electrode member, and whose reaction product readily dissolves or has high conductivity in the electrolyte solvent.

The iontophoresis electrode device according to claim 16 has the construction of claim 14 wherein the depolarizer is one or a combination of 2 or more selected from among ascorbic acid, erythorbic acid, cysteine, acetylcysteine, thioglycolic acid, thiomalic acid or their salts, sulfites, bisulfites, thiosulfates, pyrosulfites, nitrites, iodides α-thioglycerine.

The iontophoresis electrode device according to claim 17 has the construction of claim 15 wherein the depolarizer is one or a combination of 2 or more selected from among iron (III) compounds such as ferric chloride, copper (II) compounds such as copper sulfate, and hydrogen peroxide.

The iontophoresis electrode device according to claim 18 has the construction of any of claims 3 to 17, wherein the pH regulator is a basic oxide or basic hydroxide such as calcium oxide, magnesium oxide, calcium hydroxide, magnesium hydroxide or hydroxyapatite, or a mixture thereof.

The iontophoresis electrode device according to claim 19 has the construction of any of claims 3 to 17, wherein the pH regulator is a silicic acid or acid anhydride such as a silica gel, light silicic anhydride, phthalic anhydride or isobutylene-maleic anhydride copolymer, or a mixture thereof.

The iontophoresis electrode device according to claim 20 has the construction of any of claims 3 to 17, wherein the pH regulator is an amphoteric oxide, amphoteric hydroxide, aluminate, aluminosilicate or silicate or compound salt thereof, such as γ-alumina, aluminum hydroxide, dry aluminum hydroxide gel, magnesium aluminum hydroxide, aluminum glycinate, synthetic hydrotalcite, zeolite, synthetic aluminum silicate, natural aluminum silicate, magnesium aluminosilicate, magnesium aluminometasilicate, bismuth magnesium aluminosilicate, magaldrate, calcium silicate, magnesium silicate or zinc oxide, or a mixture thereof.

The iontophoresis electrode device according to claim 21 has the construction of any of claims 7 to 14, 16, 18 or 20, wherein the drug is a cationic drug.

The iontophoresis electrode device according to claim 22 has the construction of any of claims 7 to 13, 15, 17, 19 or 20, wherein the drug is an anionic drug.

The present invention exhibits the following effects based on these constructions.

Since the device is provided with an inert electrode member and a depolarizer, it is possible to avoid entrance of metal ions from the electrode into the body of the subject. In addition, because no polarization is produced it is possible to prevent reduction in the transport current and thus achieve high drug penetration.

When the device is provided with an inert electrode member, depolarizer and buffering agent, it is possible not only to avoid entrance of metal ions from the electrode into the body but also to prevent polarization. In addition, while the application time will differ depending on the transport current value when the iontophoresis electrode device is applied to a subject, no skin irritation due to pH changes is found during short application times (5 to 30 minutes) with the combination of the inert electrode member and depolarizer, but when a buffering agent is further included in the device, it is possible to avoid irritation to the skin even when the application time is extended to a medium length (30 to 90 minutes).

When the device is provided with an inert electrode member, a depolarizer and a pH regulator which is poorly soluble in the electrolyte solvent, its ion mobility is markedly higher than other ions, and therefore a very powerful effect can be produced as a competitive ion for the drug, etc., to neutralize protons and hydroxide ions and eliminate their competition with the drug ion, in order to maintain a high drug penetration dose. In addition, since the ions are only exchanged to the degree necessary for neutralization, the buffering power lasts throughout the administration, and no irritation is produced in the skin.

Furthermore, unlike a buffering solution, a poorly soluble pH regulator dissolves only the amount of ions necessary for neutralization, and can therefore minimize competition with the drug. As a result it is possible to prevent skin irritation due to pH changes even when the electrode device is applied to a subject for long periods.

Because the buffering power is prolonged and there is no skin irritation, thus allowing long-term application, it becomes possible to administer high molecular drugs which have presented problems in the past, and to satisfactorily deliver drugs which require slow administration over long periods. In addition, even with prolonged administration there is no invasion of metal ions from the electrode into the body of the subject and no polarization, so that reduction in the transport current can be prevented for a high degree of drug penetration.

Because the electrode member is inert, it can be reused any number of times if the adhesive layer, etc. used is washable. Also, if the inert electrode is made from a carbon paste it can be produced at much lower cost than conventional electrode devices of that type while productivity can be increased since the inert electrode member is obtained by simple coating of a carbon paste.

Here, the material used for the backing may be polyethylene terephthalate, polyethylene, polypropylene, vinyl chloride resin, polyurethane or laminated films thereof.

Polyethylene terephthalate and polypropylene are particularly preferred, which has low drug adsorption and water vapor permeability. Vinyl chloride resin is not preferred from an environmental standpoint because nocuous hydrogen chloride gas is generated upon combustion.

The backing used may have a shape with a round, oval, square cup or flat cross-section.

The electrode terminal may be one which can be easily connected to an external power source and easily inserted into the hole of the backing, such as one formed into a male hook, and one which can be easily sealed.

As the electrode for the inert electrode member there is used one which produces oxygen gas or chloride ion-derived chlorine gas at the anode and which produces hydrogen gas at the cathode, during electrification in solution compositions commonly used for iontophoresis electrode devices. Specifically there may be mentioned carbon, platinum, titanium or gold, nickel, etc. Among these, carbon is preferred because it is inexpensive and can increase productivity if produced from carbon paste. Also, any metal material may be used for the cathode so long as it does not undergo corrosion by the electrolyte solvent during storage. Safety can be increased with metals such as iron, aluminum and copper, since they do not elute out.

The adhesive layer used is an oily adhesive base of natural rubber, synthetic rubber, acryl, silicone, etc. to prevent water leakage through the adhesive.

When reusability is a consideration, it is preferred to use a material which is soluble in aqueous organic solvents. For reuse, the adhesive layer can be immersed in an aqueous organic solvent for simple release to allow reuse of the device.

The material used as the liner may be a synthetic resin film or sheet of polyethylene terephthalate, polypropylene, etc., a metal film of aluminum, etc., or a composite film thereof. A metal film is preferably used for reusability, because of its high mechanical strength.

The electrolyte solvent used may be any solvent of high safety which can adequately release electrolytes. Specifically there may be mentioned water, ethanol, propylene glycol, dipropylene glycol, 1,3-butylene glycol, glycerin, polyethylene glycol and polypropylene glycol, any of which may be used alone or in combinations of 2 or more.

The non-adhesive gel used is preferably agar, gelatin, xanthan gum, locust bean gum, carragheenan, pectin, glucomannan, gelan gum, tamarind gum or polyacrylamide. A crosslinking agent may also be used if necessary. For reuse, the non-adhesive gel may be removed simply by washing with water.

The depolarizer is added for the purpose of reducing polarization of the electrode, and different depolarizers are used at the anode and cathode.

It is advantageous for the anode depolarizer to be anionic at the oxidizing region since an anionic one migrates more easily toward the reaction field of the electrode surface, but a nonionic one may be used if its concentration is sufficient. In terms of equilibrium, a lower standard oxidation-reduction potential tends toward oxidation, but kinetically speaking the concentration and electrode catalytic effect also contribute, so that an effective depolarizer cannot be judged only on the standard oxidation-reduction potential. An electrode reactive substance which is preferentially oxidized over hydroxide ions and chloride ions in the prescribed system is selected.

Particularly preferred electrode reactive substances include ascorbic acid, erythorbic acid, cysteine, acetylcysteine, thioglycolic acid, thiomalic acid and their sodium and chlorine salts, hydrogensulfite such as sodium hydrogensulfite, thiosulfates such as sodium thiosulfate, pyrosulfites such as sodium pyrosulfite and potassium pyrosulfite, iodides such as potassium iodide and sodium iodide, and α-thioglycerine, among which any one or combination of 2 or more may be used.

Chemical formula 1 shows an example of a reaction on the electrode surface during electrification, wherein an inert electrode is used as the anode, sodium sulfite is used as the depolarizer and water is used as the electrolyte solvent.

As seen from chemical formula 1, the current flows without generation of oxygen. The cations which migrate in the direction of the skin are sodium ions and protons. This type of depolarizer is an oxygen-incorporating reducer which acquires oxygen from water and generates protons, but there may also be mentioned hydrogensulfite such as sodium hydrogensulfite, thiosulfate salts such as sodium thiosulfate, pyrosulfite salts such as sodium pyrosulfite and potassium pyrosulfite, and nitrite salts such as sodium nitrite.

Chemical formula 2 shows another example of an electrochemical reaction on the electrode surface during electrification, wherein an inert electrode is used as the anode, sodium thioglycolate is used as the depolarizer and water is used as the electrolyte solvent.

As seen from chemical formula 2, the current flows without generation of oxygen. The cations which flow in the direction of the skin here are sodium ions and protons. This type of depolarizer is a hydrogen- or metal ion-releasing reducer which releases a proton if the oxidized functional group includes a dissociating hydrogen or releases a metal ion when it includes a metal, but there may also be mentioned ascorbic acid, erythorbic acid, cysteine, acetylcysteine, thiomalic acid and their salts, as well as α-thioglycerine, thioglycolic acid and thiourea. Because these compounds have dissociating hydrogen in the functional groups which contribute to the oxidation-reduction reaction or in other functional groups, any of these depolarizers may be selected for migration of protons in the direction of the skin during electrification.

Chemical formula 3 shows yet another example of a reaction on the electrode surface during electrification, wherein an inert electrode is used as the anode, potassium iodide is used as the depolarizer and water is used as the electrolyte solvent.

As seen from chemical formula 3, the current flows without generation of oxygen. The iodine generated in chemical formula 3 binds with iodide ion, becoming soluble. The cation which migrates in the direction of the skin here is potassium ion. Thus, no hydrogen ion is generated in the oxidation reaction occurring with the valency increase of each atom.

Also, it is advantageous for the cathode depolarizer to be cationic at the reducing portion, conversely to the anode, since a cationic one migrates more easily toward the reaction field of the electrode surface, but a nonionic one may also be used if its concentration is sufficient.

Like the anode depolarizer, an effective depolarizer cannot be judged only on the standard oxidation-reduction potential. An electrode reactive substance which is preferentially reduced over hydrogen ions in the prescribed system is selected. However, when carbon is used for the inert electrode member, a strong oxidizing agent should not be used since carbon is relatively easily oxidized.

Particularly preferred electrode reactive substance; include iron (III) compounds such as ferric chloride and iron citrate, copper (II) compounds such as copper sulfate, copper gluconate and copper citrate, and hydrogen peroxide, among which any one or a combination of 2 or more may be used. Chemical formula 4 shows an example of an electrochemical reaction on the electrode surface during electrification, wherein an inert electrode is used as the anode, ferric chloride is used as the depolarizer and water is used as the electrolyte solvent.

As seen from chemical formula 4, the current flows without generation of hydrogen. The anion which flows in the direction of the skin here is chloride ion. Thus, no generation of: hydroxide ion is seen in the reduction reaction represented by the valency decrease of each atom. When the ion opposing the metal ion is hydroxide ion, hydroxide ion migrates in the direction of the skin. Other oxidizing agents include copper (II) compounds such as copper sulfate, copper gluconate and copper citrate, as well as iodine, but iodine is not preferred because it is reduced to the anion which invades the human body.

Copper (II) ions are reduced to copper (I) ions or metallic copper, but metallic copper does not produce polarization because of its high conductivity even which insoluble in the electrolyte solution.

Chemical formula 5 shows another example of an electrochemical reaction on the electrode surface during electrification, wherein an inert electrode is used as the cathode, hydrogen peroxide is used as the depolarizer and water is used as the electrolyte solvent.

As seen from chemical formula 5, the current flows without generation of hydrogen. The anion which flows in the direction of the skin here is hydroxide ion. Thus, in addition to such cation (proton, in this case)—incorporating oxidizing agents, reactive oxygen-releasing oxidizing agents such as potassium permanganate also release hydroxide ions.

Such depolarizers among these which are ionic can also be present as the counter ion of the ion-exchange resin.

The pH regulator is preferably one which is poorly soluble in the electrolyte solvent. When the electrode device is connected to an anode, a basic compound or amphoteric compound is used, and when the electrode device is connected to a cathode, an acidic compound or amphoteric compound is selected. Suitable basic compounds include basic oxides such as calcium oxide, magnesium oxide, silver oxide, chromous oxide, iron monoxide, iron sesquioxide, bismuth trioxide, manganese monoxide and copper monoxide, and basic hydroxides such as calcium hydroxide, magnesium hydroxide, chromium hydroxide, cobalt hydroxide, ferrous hydroxide, cupric hydroxide, nickel hydroxide, bismuth hydroxide, manganese hydroxide and hydroxyapatite; preferred among these are calcium oxide, magnesium oxide, calcium hydroxide, magnesium hydroxide and hydroxyapatite. Calcium and magnesium are relatively abundant in the body and therefore their slight migration into the body has no adverse effect.

The neutralization reaction of the basic compound and the acid will now be explained with chemical formula 6 for the example of calcium oxide.

As seen from chemical formula 6, calcium oxide has low solubility in the range from neutral to basic, and neutralization reaction only occurs with approach of a proton causing dissolution of calcium ion, whereby charge migration is exchanged from the proton to the calcium ion.

The acidic compound used may be an acid anhydride, for example, silicic acid and its anhydrides such as silica gel, orthosilicic acid, light silicic anhydride, quartz, etc., and particularly preferred among these are silica gel, light silicic anhydride, phthalic anhydride and isobutylene-maleic anhydride copolymer. Silica gel and light silicic anhydride have high reactivity, while succinic anhydride and the like are easily hydrolyzed with water, and so their use is particularly preferred.

The neutralizing reaction for the acidic compound and the base will now be explained with chemical formula 7 for the example of phthalic anhydride. (Ph in the formula represents ortho-phenylene.)

As seen from chemical formula 7, phthalic anhydride has low solubility in the range near neutral, and neutralization reaction only occurs with approach of hydroxide ion causing dissolution of phthalate ion, whereby charge migration is exchanged from the hydroxide ion to the phthalate ion.

Also, an amphoteric oxide or amphoteric hydroxide, aluminate, aluminosilicate, silicate or a compound salt thereof may also be selected, among which there are particularly preferred γ-alumina, aluminum hydroxide, dry aluminum hydroxide gel, magnesium aluminum hydroxide, aluminum glycinate, synthetic hydrotalcite, zeolite, synthetic aluminum silicate, natural aluminum silicate, magnesium aluminosilicate, magnesium aluminometasilicate, bismuth magnesium aluminosilicate, magaldrate, calcium silicate, magnesium silicate and zinc oxide, as well as antimony oxide, lead trioxide, germanium oxide, tin oxide and gallium hydroxide. These metal ions are highly safe.

The neutralization reaction for an amphoteric compound and acid will now be explained with chemical formula 8 for the example of magnesium aluminometasilicate.

As seen from chemical formula 8, magnesium aluminometasilicate has low solubility in the range near neutral, and therefore neutralization reaction only occurs with approach of a proton causing dissolution of aluminum and magnesium ions, whereby charge migration is exchanged from the proton to the aluminum and magnesium ions.

The neutralization reaction for an amphoteric compound and base will now be explained with chemical formula 9 for the example of aluminum hydroxide.

As seen from chemical formula 9, aluminum hydroxide has low solubility in the range near neutral, and therefore neutralization reaction only occurs with approach of a hydroxide ion causing dissolution of aluminate ion, whereby charge migration is exchanged from the hydroxide ion to the aluminate ion.

The amount of the depolarizer and pH regulator to be added is preferably in the range of $10^{-8}$ to $10^{-2}$ gram equivalents.

The drug used may be any drug applied in the field of therapy so long as it dissolves and dissociates in the electrolyte solvent, and in particular, drugs of molecular weight $10^2$ to $10^6$ are widely used.

As drug groups there may be mentioned antimicrobial agents, anticancer drugs, hormonal agents, antiallergic agents, hepatic disease agents, diabetic therapy agents, metabolic medicines, blood agents, anti-inflammatory agents, CNS acting drugs, peripheral nerve agents, circulatory drugs, respiratory drugs, gastrointestinal drugs, narcotic drugs, polakisuria therapy agents, and the like.

Drugs which can dissociate into cations include, but are not limited to, bacampicillin, sultamicillin, cefpodoximeproxetil, cefterampivoxil, cefmenoxime, cefotiam, doxycycline, minocycline, tetracycline, erythromycin, rokitamycin, amikacin, arbekacin, astromicin, dibekacin, gentamycin, isepamycin, kanamycin, micronomicin, sisomycin, streptomycin, tobramycin, ethambutol, isoniazid fluconazole, flucytosine, miconazole, aciclovir, chloramphenicol, clindamycin, fosfomycin, vancomycin, aclarubicin, bleomycin, cytarabin, dacarbazine, nimustine, peplomycin, procarbazine, vinblastine, vincristine, vindesine, calcitonin, parathyroid hormone (PTH), granulocyte colony-stimulating factor (G-CSF), mecasermin, alimemazine, chlorpheniramine, clemastine, mequitazine, azelastine, ketotifen, oxatomide, methylmethionine sulfonium chloride, colchicine, camostat, gabexate, nafamostat, mizoribine, piroxicam, proglumetacin, emorfazone, tiaramide, buprenorphine, ergotamine, phenacetin, rilmazafone, triazolam, zopiclone, nitrazepam, clonazepam, amantadine, bromocriptine, chlorpromazine, sultopride, chlordiazepoxide, cloxazolam, diazepam, etizolam, oxazolam, amitriptyline, imipramine, nortriptyline, setiptiline, ticlopidine, atropine, scopolamine butylbromide, eperisone, pancuronium bromide, tizanidine, pyridostigmine bromide, dobutamine, dopamine, benidipine, diltiazem, nicardipine, verapamil, acebutolol, atenolol, carteolol, metoprolol, nipradilol, pindolol, propranolol, dipyridamole, nicorandil, tradipil, ajmaline, aprindine, cibenzoline, disopyramide, flecainide, isoprenaline, lidocaine, mexiletine, procaine, procainamide, tetracaine, dibucaine, propafenon, quinidine, hydrochlorothiazide, trichlorothiazide, tripamide, azosemido, amosulalol, budralazine, bunazosin, cadralazin, clonidine, delapril, enalapril, guanethidine, hydralazine, labetalol, prazosin, reserpine, terazosin, urapidil, nicomol, epinephrine, etilefrine, midodrine, papaverine, clenbuterol, genoterol, mabuterol, procaterol, salbutamol, terbutaline, tulobuterol, tipepidine, ambroxol, bromhexine, cimetidine, famotidine, ranitidine, roxatidine acetate, benexate, Omepral (trade name), pirenzepine, sulpiride, cisapride, domperidone, metoclopramide, trimebutine, codeine, morphine, fentanyl, pethidine, oxybutynin, ritodrine, teroziline and their salts.

Drugs which can dissociate into anions include, but are not limited to, amoxicillin, ampicillin, aspoxicillin, benzylpenicillin, methicillin, piperacillin, sulbenicillin, ticarcillin, cefaclor, cefadroxil, cefalexin, cefatrizine, cefixime, cefradine, cefroxadine, cefamandole, cefazolin, cefmetazole, cefminox, cefoperazon, cefotaxime, cefotetan, cefoxitin, cefpiramide, cefsulodin, ceftazidime, ceftizoxime, ceftriaxone, cefzonam, aztreonam, carumonam, futmoxef, imepenem, thalamoxef, ciprofloxacin, enoxacin, nalidixic acid, norfloxacin, ofloxacin, vidrabine, fluorouracil, methotrexate, dexamethasone sodium phosphate, levothyroxine, liothyronine, amlexanox, cromoglicate, tranilast, gliclazide, insulin, benzbromarone, carbazochrome, tranexamic acid, alclofenac, aspirin, diclofenac, ibuprofen, indometacin, ketoprofen, mefenamic acid, sulindac, tiaprofenic acid, tolmetin, sulpyrine, lobenzarit, penicillamine, amobarbital, pentobarbital, phenobarbital, thiopental, phenytoin, valproate, droxidopa, levodopa, baclofen, dantrolene, denopamine, furosemide, acetazolamide, bumetanid, canreno acid, ethacrynic acid, alacepril, captopril, lisinopril, methyldopa, clofibrate, pravastatin, probucol, alprostadil, aminophylline, theophylline, carbocisteine, and their salts.

In addition, gelating agents, adhesive agents, edetic acid and other stabilizers, preservatives, absorption promoters, surfactants, and pH regulators for adjusting the initial pH may also be combined therewith if necessary.

The holding material used may be any film, woven fabric or nonwoven fabric having low adhesion for the depolarizer and drug, with a mesh size which allows sufficient migration of the electrolyte solvent from the device to the skin. Examples of such materials include polypropylene, polyethylene, polyethylene terephthalate, cellulose acetate, cellulose, polyvinylidene fluoride, hydrophilic polyvinylidene fluoride, polytetrafluoroethylene, hydrophilic polytetrafluoroethylene, polysulfone, nylon, etc., and the form thereof may be selected from among nonwoven fabrics, filter paper, membrane filters, porous films, etc., either with as a single material or as a composite or coated type.

The powder mixture is most preferably one with a particle size of no greater than 200 μm. This is effective for increasing the neutralization reaction rate of the pH regulator and the dissolution rate of the depolarizer and drug.

The coating material may be any film, woven fabric or nonwoven fabric having low adhesion for the depolarizer and drug and having a mesh size which allows sufficient migration of the electrolyte solvent from the device to the skin without letting the powder mixture pass through, and specifically the materials and forms mentioned above for the holding material may be suitably used.

The stopper used may be natural rubber, isoprene rubber, polyisobutylene rubber, styrene-alkene-styrene block copolymer-based rubber, silicone-based rubber, acrylic-based rubber or the like, which are inert in electrolyte solvents.

Suitable materials for use as the self-adhesive gel layer include karaya gum, polyvinyl alcohol, polyvinylpyrrolidone, methoxyethylene-maleic anhydride copolymer, isobutylene-maleic anhydride copolymer, polyacrylic acid, sodium polyacrylate, carboxyvinyl polymer, N-vinylacetamide-sodium acrylate copolymer, urethane-based adhesives and their combinations. The safety of these base components has been confirmed by safety tests with pharmaceuticals or medical tools.

BEST MODE FOR CARRYING OUT THE INVENTION

Preferred modes of the invention will now be explained with reference to the attached drawings.

(Mode 1)

Figure 1:
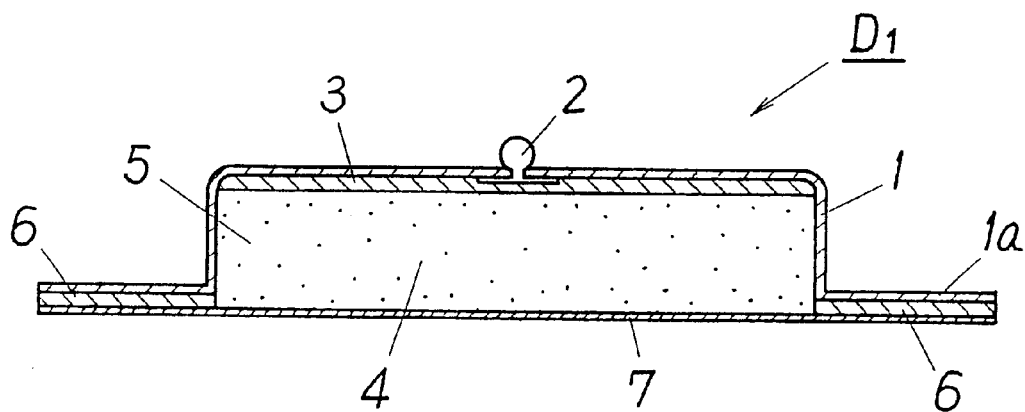
FIG. 1 is a cross-sectional view showing a major part of an iontophoresis electrode device according to a first mode of the invention.

FIG. 1 is a cross-sectional view showing a major part of an iontophoresis electrode device according to a first mode of the invention.

$D_1$ is an iontophoresis electrode device according to the first preferred mode, comprising the necessary components selected from among depolarizers, pH regulators, drugs, etc. dissolved or dispersed in a non-adhesive gel, 1 is a backing made of a non-conductive synthetic resin such as polyethylene terephthalate (hereunder, "PET") formed into a cup shape and provided with an edge section 1a outside an opening, 2 is an electrode terminal formed into a male hook shape inserted as a protrusion in the hole opened at the ceiling of the backing 1, 3 is an inert electrode situated at the ceiling of the backing 1 and laid in electrical connection with the base of the electrode terminal 2, 4 is a packing chamber formed by the hollow under the backing 1, 5 is a non-adhesive gel geled with a geling agent packed into the packing chamber 4 together with one or more of a depolarizer, pH regulator and drug dispersed or dissolved in an electrolyte solvent, 6 is an adhesive layer laminated on the outside of the edge 1a of the backing 1, and 7 is a liner attached to the adhesive layer 6 and covering the opening of the backing 1.

A method for producing and using this mode of the iontophoresis electrode device having the construction described above will now be explained.

A hole is opened in the ceiling of the packing chamber 4 of a cup-shaped backing 1 made of non-conductive plastic and formed with a molding machine, and a male hook-shaped electrode terminal 2 is positioned therein. An inert electrode 3 is inserted or printed on the ceiling of the packing chamber 4 so as to cover up the base of the electrode terminal 2. Next, the adhesive layer 6 is laminated on the edge 1a of the backing 1. The packing chamber 4 is then packed with a non-adhesive gel 5 such as agar or the like, and the liner 7 is laminated over the adhesive layer 6.

For use, the liner 7 is peeled off, and after attachment to the skin or mucous membrane, the electrode terminal 2 is connected to a circuit to begin electrification.

Since an inert electrode is used as the electrode in the mode described above, the metal ions from the electrode do not enter the body of the subject. Also, because the electrode is inert it can be reused to allow economy of resources. The electrode can also be made from carbon paste for high productivity and yields, to allow mass production at low cost.

When the inert electrode is combined with a depolarize, elimination of polarization makes it possible to prevent reduction in transport current and to achieve high drug penetration. It is also possible to prevent skin irritation due to pH changes even during electrification for reactions involving valency change of a single atom. In systems in which the pH changes during electrification, addition of a buffering agent can further prolong the application time. However, it has been found that buffering power sometimes decreases with long-term application.

When the non-adhesive gel is provided with a depolarizer and a pH regulator which is poorly soluble in electrolyte solvents, the poorly soluble pH regulator dissolves out just enough ions necessary for neutralization, unlike a buffering agent, so that competition with the drug can be minimized.

A sustained effect can thus be achieved from both the standpoints of safety and effectiveness. As a result, it is possible to avoid skin irritation due to pH changes even with prolonged application of the electrode device to subjects.

Because prolonged application is possible, conventionally problematic high molecular drugs can be administered, while the device can also be applied for drugs which require gradual administration over long periods. In addition, metal ions from the electrode do not enter the body of the subject even with prolonged administration, and since no polarization occurs it is possible to prevent reduction in transport current to achieve higher drug delivery.

(Mode 2)

Figure 2:
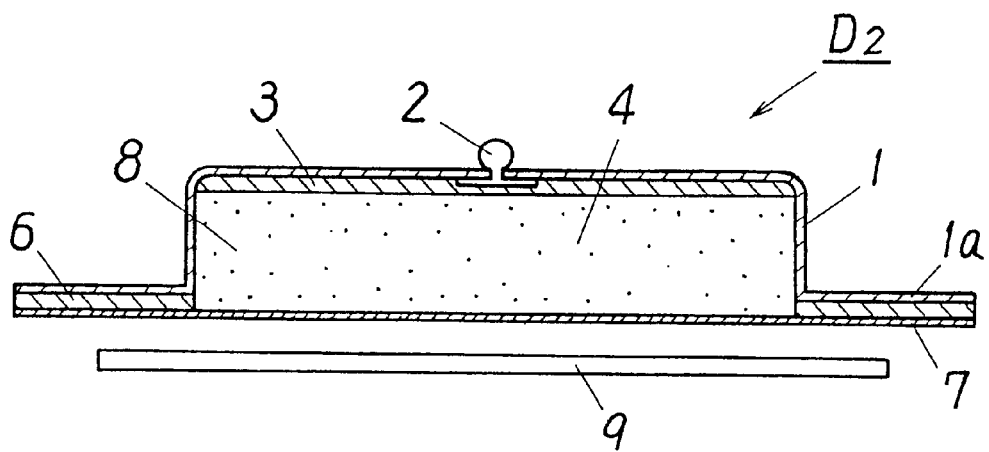
FIG. 2 is a cross-sectional view showing a major part of an iontophoresis electrode device according to a second mode of the invention.

FIG. 2 is a cross-sectional view showing a major part of an iontophoresis electrode device according to a second mode of the invention.

Numeral 1 is the backing, 1a is the edge, 2 is the electrode terminal, 3 is the inert electrode, 4 is the packing chamber, 6 is the adhesive layer and 7 is the liner, and since these are identical to the first mode they are indicated by like reference numerals and their explanation will be omitted.

$D_2$ is the iontophoresis electrode device according to the second mode, which is formed as a type wherein a pH regulator is dispersed in the non-adhesive gel if necessary, and when a depolarizer and/or drug which is unstable in the electrolyte solvent is used these unstable substances are held in a dry state in a holding material, with the holding material and non-adhesive gel contacted immediately prior to application, 8 is a non-adhesive gel geled with a geling agent and if necessary a pH regulator dispersed or dissolved in an electrolyte solvent, and 9 is a holding material made of filter paper, a nonwoven fabric, membrane filter, porous film or the like, holding a depolarizer or drug which is unstable in the electrolyte solvent.

A method for producing and using the second mode of the iontophoresis electrode device having the construction described above will now be explained.

The electrode terminal 2, inert electrode member 3 and adhesive layer 6 are provided on the backing 1 and the packing chamber 4 in the same manner as the first mode.

The non-adhesive gel 8 is packed into the packing chamber 4, and the liner 7 is laminated on the adhesive layer 6 to complete the production.

For use, the liner 7 is peeled off, the holding material 9 already holding the unstable depolarizer and/or drug is attached so as to cover the surface of the non-adhesive gel 8 while contacting therewith, and after attachment to the skin or mucous membrane in a manner allowing contact with the adhesive layer 6 of the iontophoresis electrode device $D_2$, the iontophoresis electrode terminal 2 is connected to a circuit to begin electrification.

According to the mode described above, it is possible to provide the effect achieved by the first mode, as well as that of extending the usable life of preparations containing depolarizers and/or drugs which are unstable during prolonged contact with electrolyte solutions or under the heat of production, thus notably improving their durability.

(Mode 3)

Figure 3:
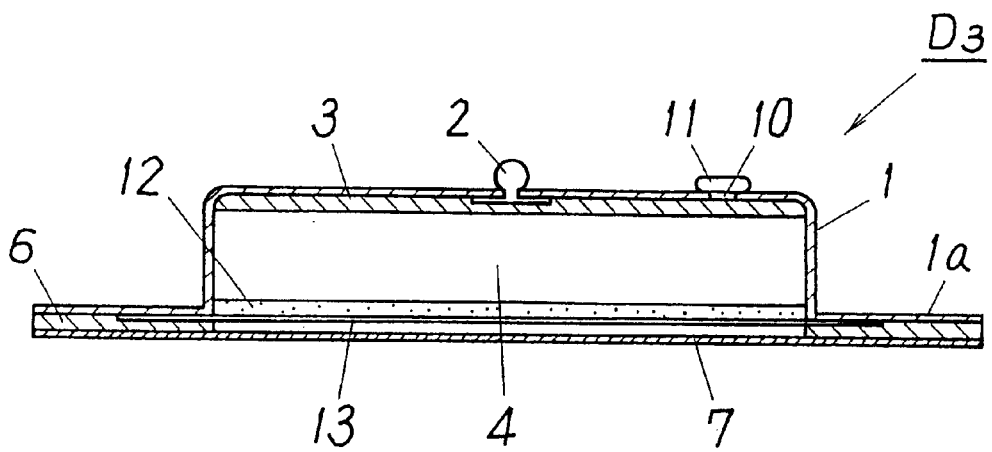
FIG. 3 is a cross-sectional view showing a major part of an iontophoresis electrode device according to a third mode of the invention.

FIG. 3 is a cross-sectional view showing a major part of an iontophoresis electrode device according to a third mode of the invention.

Numeral 1 is the backing, 1a is the edge, 2 is the electrode terminal, 3 is the inert electrode, 4 is the packing chamber, 6 is the adhesive layer and 7 is the liner, and since these are identical to the first mode they are indicated by like reference numerals and their explanation will be omitted.

$D_3$ is the iontophoresis electrode device according to the third mode, wherein the packing chamber 4 encloses a drug, depolarizer and/or a pH regulator which is poorly soluble in electrolyte solvents, and an electrolyte solvent or an electrolyte solution in which the depolarizer and drug are dissolved in an electrolyte solvent is supplied just prior to application, 10 is an injection opening formed in the ceiling of the packing chamber 4 through the backing 1, 11 is a stopper made of rubber or the like which provides a sealing function to prevent leakage of the electrolyte solvent or electrolyte solution injected through the injection hole 10 and also allows insertion of an injection needle for injection of the electrolyte solvent or electrolyte solution, 12 is a powder mixture selected from among powdered depolarizer, pH regulators and drugs which are weighed and loaded into the packing chamber 4, and 13 is an ion permeable covering which covers the opening of the backing 1 to prevent leakage of the electrolyte solvent or electrolyte solution during application while allowing permeation of ions.

A method for producing and using the third mode of the iontophoresis electrode device having the construction described above will now be explained.

The electrode terminal 2 and inert electrode member 3 are provided on the backing 1 in the same manner as the first mode, together with the injection opening 10.

The stopper 11 is then inserted into the injection opening 10. The powder mixture 12 is loaded on the inner side of the backing 1. The entire opening of the packing chamber 4 is covered with an ion permeable covering 13 which prevents sudden leakage of the electrolyte solvent or electrolyte solution during application and whose perimeter is embedded in the edge section 1a with a formed adhesive layer 6, and a liner 7 is laminated thereover.

For use, a sufficient amount of the electrolyte solvent or electrolyte solution is injected through the stopper 11 via an injection tube housing an injection needle, to fill the packing chamber 4. The liner 7 is peeled off, and after attachment to the skin or mucous membrane, the electrode terminal 2 is connected to a circuit to begin electrification.

According to the mode described above, it is possible to provide the effect achieved by Modes 1 and 2, as well as that of a more rapid buildup of transport current than with the second mode, since the depolarizer and inert electrode member are in contact from the initial moment of application.

(Mode 4)

Figure 4:
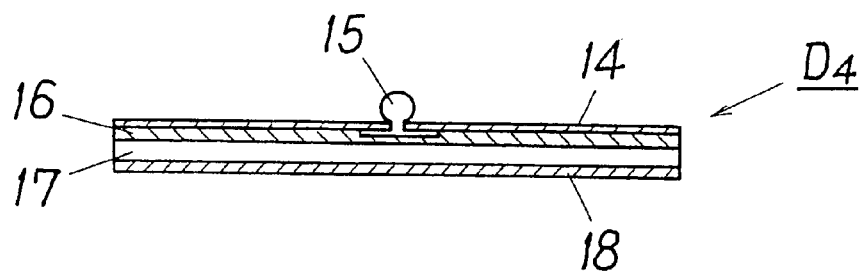
FIG. 4 is a cross-sectional view showing a major part of an iontophoresis electrode device according to a fourth mode of the invention.

FIG. 4 is a cross-sectional view showing a major part of an iontophoresis electrode device according to a fourth mode of the invention.

$D_4$ is the iontophoresis electrode device according to the fourth mode wherein the necessary components selected from among depolarizers, pH regulators and drugs are dissolved or dispersed in an self-adhesive gel, 14 is a backing made of a non-conductive synthetic resin formed into a sheet or film, 15 is an electrode terminal inserted as a protrusion in an electrode terminal-insertion hole of the backing 14, 16 is an inert electrode situated on the back side of the backing 14 and laid in electrical connection with the base of the electrode terminal 15, 17 is an self-adhesive gel formed by gelating the dispersion/solution of the gelating agent, depolarizer, pH regulators and drug in the electrolyte solvent, and 18 is a liner covering the surface of the self-adhesive gel 17.

A method for producing and using the fourth mode of the iontophoresis electrode device having the construction described above will now be explained.

A hole is opened in the ceiling of the film-like backing 14 of the iontophoresis electrode device $D_4$ and a male hook-shaped electrode terminal 15 is inserted therein. An inert electrode member 16 is mounted or printed on the ceiling of the backing 14 so as to cover up the electrode terminal 15. The self-adhesive gel 17 formed by gelating the dispersion/solution of the gelating agent, depolarizer, pH regulators and drug in the electrolyte solvent is laminated on the surface of the inert electrode member 16 and the liner 18 is further laminated thereon.

For use, the liner 18 is peeled off, and after attachment to the skin or mucous membrane the electrode terminal 15 is connected to a circuit to begin electrification.

According to the mode described above, it is possible to provide the effect achieved by the first mode, as well as that of reducing the application area, simplifying the shape and providing adhesion over the entire application surface, so that loss of the preparation can be minimized for increased productivity.

The invention will now be explained in more detail by way of embodiments, examples and experimental examples.

(Embodiment 1)

A polyethylene terephthalate (hereunder abbreviated to PET) cup-shaped backing was prepared with an outer diameter of 40 mm, an inner diameter of 30 mm, a depth of 1.5 mm and a thickness of 200 $\mu$m, having a hole opened in the ceiling and the protruding section of an electrode terminal inserted therein. An inert electrode member made of carbon paste DY-280L-3 (product of Toyo Spinning, KK.) was coated to cover the base of the electrode terminal on the ceiling of the packing chamber as a disk with a thickness of 300 $\mu$m and a diameter of 28 mm, after which it was dried with a box drier at a drying temperature of 60° C. for 30 minutes and 100° C. for 45 minutes, to obtain an iontophoresis electrode. The thickness of the carbon section of the inert electrode fabricated in this manner was 150 $\mu$m.

(Embodiment 2)

A backing was fabricated by opening a hole in a 75 $\mu$m-thick PET film and inserting the protruding section of an electrode terminal therein. The base of the electrode terminal on the back side was then coated with carbon paste DY-280L-3 (product of Toyo Spinning, KK.) to a thickness of 300 $\mu$m to form an inert electrode member, after which it was dried with a box drier at a drying temperature of 60° C. for 30 minutes and 100° C. for 45 minutes. It was then cut into an appropriate shape to obtain the iontophoresis electrode for this embodiment. The thickness of the carbon section of the inert electrode fabricated in this manner was 150 $\mu$m.

(Embodiment 3)

The iontophoresis electrode for this embodiment was obtained in the same manner as Embodiment 1, except that a disk-shaped platinum film with a diameter of 28 mm and a thickness of 50 $\mu$m was used as the inert electrode member and it was attached to the base of the electrode terminal of the packing chamber with double-sided adhesive tape.

(Embodiment 4)

The iontophoresis electrode for this embodiment was obtained in the same manner as Embodiment 2, except that a platinum film with a thickness of 40 $\mu$m was used as the inert electrode member and it was attached to the base of the electrode terminal with double-sided adhesive tape.

(Embodiment 5)

The iontophoresis electrode for this embodiment was obtained in the same manner as Embodiment 1, except that a disk-shaped titanium film with a diameter of 28 mm and a thickness of 50 $\mu$m was used as the inert electrode member and it was attached to the base of the electrode terminal of the packing chamber with double-sided adhesive tape.

(Embodiment 6)

The iontophoresis electrode for this embodiment was obtained in the same manner as Embodiment 2, except that a titanium film with a thickness of 40 $\mu$m was used as the inert electrode member and it was attached to the base of the electrode terminal with double-sided adhesive tape.

(Embodiment 7)

A backing was fabricated by opening a hole in a 75 $\mu$m-thick PET film and inserting the protruding section of an electrode terminal therein. An inert electrode member was also fabricated, using as the anode one side of a 40 $\mu$m-thick silver film attached to double-sided adhesive tape and as the electrolyte solution a 0.9% aqueous solution of sodium chloride, passing through a direct current of 0.5 mA/cm$^2$ for 4 hours, washing off the produced AgCl/Ag and then drying at 60° C. for 3 hours. The release sheet on the double-sided adhesive tape of the inert electrode member was peeled off for attachment onto the base of the electrode terminal to obtain the iontophoresis electrode for this embodiment.

(Embodiment 8)

A cup-shaped PET backing was fabricated having an outer diameter of 40 mm, an inner diameter of 30 mm, a depth of 1.5 mm and a thickness of 200 $\mu$m, with a hole opened in the ceiling and the protruding section of an electrode terminal inserted therein. An inert electrode member was also fabricated, using as the anode one side of a 40 $\mu$m-thick silver film attached to double-sided adhesive tape and as the electrolyte solution a 0.9% aqueous solution of sodium chloride, passing through a direct current of 0.5 mA/cm$^2$ for 4 hours, washing off the produced AgCl/Ag and then drying at 60° C. for 3 hours. The release sheet of the double-sided adhesive tape on the inert electrode member was peeled off for attachment onto the base of the electrode terminal of the packing chamber to obtain the iontophoresis electrode for this embodiment.

(Embodiment 9)

The iontophoresis electrode for this embodiment was obtained in the same manner as Embodiment 2, except that a silver film with a thickness of 40 $\mu$m was used as the inert electrode member and it was attached to the base of the electrode terminal with double-sided adhesive tape.

(Embodiment 10)

The iontophoresis electrode for this embodiment was obtained in the same manner as Embodiment 1, except that a disk-shaped silver film with a diameter of 28 mm and a thickness of 50 $\mu$m was used as the inert electrode member and it was attached to the base of the electrode terminal of the packing chamber with double-sided adhesive tape.

(Embodiments 11 to 28)

Electrolyte solutions for Embodiments 11 to 28 were prepared with the compositions listed in Table 1, and each of the depolarizers was dissolved in purified water at room temperature as the electrolyte solvent to a total of 100 g.

(Embodiments 29 to 49)

Electrolyte solutions for Embodiments 29 to 49 were prepared with the compositions listed in Tables 2 and 3, and each of the anode pH regulators and depolarizers were dissolved in purified water at room temperature as the electrolyte solvent to a total of 100 g, forming uniform dispersions.

(Embodiments 50 to 69)

Electrolyte solutions for Embodiments 50 to 69 were prepared with the compositions listed in Tables 4 and 5, and each of the cathode pH regulators and 2.5 ml of 30% aqueous solution of hydrogen peroxide as the depolarizer were mixed with purified water at room temperature as the electrolyte solvent to a total of 100 g, forming uniform dispersions.

EXAMPLES 1 to 20

Cylindrical cells each with an inner diameter of 17.8 mm and an electrode distance of 5 mm were prepared, and after the iontophoresis electrode of Embodiment 2, 4 or 6 which had been cut into a disk of 22 mm diameter was fixed to one side with double-sided adhesive tape and 1.25 ml of one of the electrolyte solutions of Embodiments 11–28 listed in Table 1 was filled into the cell, a release-treated PET film which had been cut into a disk of 22 mm diameter was fixed to the other side of each cell as a liner with double-sided adhesive tape, to fabricate iontophoresis electrode devices for Examples 1 to 20 in the combinations listed in Table 6.

EXAMPLES 21 to 61

After the iontophoresis electrode of Embodiment 2 which had been cut into a disk of 22 mm diameter was fixed to one side of each cylindrical cell with an inner diameter of 17.8 mm and an electrode distance of 5 mm with double-sided adhesive tape and 1.25 ml of one of the electrolyte solutions of embodiments listed in Tables 2 to 5 was filled into each cell, a release-treated PET film which had been cut into a disk of 22 mm diameter was fixed to the other side of each cell as a liner with double-sided adhesive tape, to fabricate iontophoresis electrode devices for Examples 21 to 61 in the combinations listed in Tables 7 and 8.

EXAMPLE 62

| | |
|---|---|
| Sodium sulfite | 21.0 g |
| Calcium silicate | 26.0 g |
| Tetracaine hydrochloride | 60.0 g |
| Total | 107.0 g |

The powdered materials listed above were provided and thoroughly mixed to prepare a powder mixture. After attaching a 5 mm-diameter, 1 mm-thick silicone rubber piece as a stopper into the ceiling of a cup-shaped backing of an iontophoresis electrode according to Embodiment 1, 107 mg of the powder mixture was loaded into the packing chamber, and then after affixing donut-shaped double-sided adhesive tape with an outer diameter of 40 mm and an inner diameter of 30 mm to the edge section, the release paper was peeled off, 34 mm-diameter disk-shaped filter paper was adhered thereto as an ion permeable coating material, and a 44 mm-diameter, 75 μm-thick PET film which had been release-treated was used as a liner and attached to the released side, to obtain an iontophoresis electrode device for Example 62. Purified water was provided as the electrolyte solvent, and upon application it was injected through the stopper with a 1 ml needle-equipped injection syringe for dissolution of the powder mixture.

EXAMPLE 63

| | |
|---|---|
| Ascorbic acid | 2.0 g |
| Dry aluminum hydroxide gel | 0.8 g |
| Tetracaine hydrochloride | 6.0 g |
| Agar | 1.0 g |
| Purified water | 90.2 g |
| Total | 100.0 g |

The materials listed above were provided, the agar was heated to dissolution as a gelating agent in half the amount of purified water of the materials, and upon reaching 60° C. a dispersion solution of the ascorbic acid, dry aluminum hydroxide gel and tetracaine hydrochloride which had been previously dissolved, dispersed and heated to 60° C. in the remaining purified water was added thereto to prepare a test agent. After packing 1.0 g of the test agent into the packing chamber of a cup-shaped iontophoresis electrode according to Embodiment 1 which had donut-shaped double-sided adhesive tape with an outer diameter of 40 mm and an inner diameter of 30 mm attached to the edge section, the test agent was cooled to solidity. Next, a 44 mm-diameter, 75 μm-thick PET film which had been release-treated was used as a liner and its released side was adhered to the edge section of the opening of the backing via double-sided adhesive tape, to obtain the iontophoresis electrode device for Example 63.

EXAMPLE 64

The iontophoresis electrode device for Example 64 was fabricated by the same method as Example 61, except that an iontophoresis electrode according to Embodiment 3 was used.

EXAMPLE 65

The iontophoresis electrode device for Example 65 was fabricated by the same method as Example 61, except that an iontophoresis electrode according to Embodiment 5 was used.

EXAMPLE 66

| | |
|---|---|
| Ascorbic acid | 2.0 g |
| Tetracaine hydrochloride | 6.0 g |
| Agar | 1.0 g |
| Purified water | 91.0 g |
| Total | 100.0 g |

The materials listed above were provided, the agar was heated to dissolution in half the amount of purified water of the materials, and upon reaching 60° C. a solution of the ascorbic acid and tetracaine hydrochloride which had been previously dissolved and heated to 60° C. in the remaining purified water was added thereto to prepare a test agent. After packing 1.0 g of the test agent into the packing chamber of the cup-shaped backing of an iontophoresis electrode according to Embodiment 1 which had donut-shaped double-sided adhesive tape with an outer diameter of 40 mm and an inner diameter of 30 mm attached to the bottom, the test agent was cooled to solidity. Next, a 44 mm-diameter, 75 µm-thick PET film which had been release-treated was used as a liner and its released side was adhered to the edge section of the opening of the backing via the tape, to fabricate the iontophoresis electrode device for this example.

EXAMPLE 67

| | |
|---|---|
| Isobutylene-maleic anhydride copolymer | 20.0 g |
| Sodium hydroxide | 3.0 g |
| Purified water | 36.0 g |
| Propylene glycol | 30.0 g |
| Erythorbic acid | 2.0 g |
| Tetracaine hydrochloride | 6.0 g |
| Magnesium aluminometasilicate | 1.5 g |
| Diethylene diglycidyl ether | 1.5 g |
| Total | 100.0 g |

The materials listed above were provided, the isobutylene-maleic anhydride copolymer and sodium hydroxide was heated to dissolution in the purified water of the materials, and after cooling, the propylene glycol, erythorbic acid, tetracaine hydrochloride, magnesium aluminometasilicate and diethylene diglycidyl ether were added in a nitrogen atmosphere to prepare a mixed and dispersed test agent. The test agent was applied onto the released side of a 75 µm-thick PET film to a thickness of 1.5 mm, and after affixing it to an iontophoresis electrode according to Embodiment 2 and allowing it to stand in a nitrogen atmosphere at 60° C. for 24 hours, it was cut into a 30 mm-diameter disk to obtain the iontophoresis electrode device for this example.

EXAMPLE 68

| | |
|---|---|
| Calcium silicate | 1.5 g |
| Gelan gum | 1.0 g |
| Purified water | 97.5 g |
| Total | 100.0 g |

The materials listed above were provided, and after heating the agar to dissolution in the purified water of the materials, the temperature was lowered to 70° C., the calcium silicate was added and the mixture was uniformly dispersed to prepare a test agent. After packing 1.0 g of the test agent into the cup-shaped packing chamber of an iontophoresis electrode according to Embodiment 1 which had donut-shaped double-sided adhesive tape with an outer diameter of 40 mm and an inner diameter of 30 mm attached to the edge section, it was cooled to solidity. Next, a 44 mm-diameter, 75 µm-thick PET film which had been release-treated was used as a liner and its released side was adhered to the edge section of the backing via double-sided adhesive tape. Separately, 10 µl of a 0.04%, aqueous solution of salmon calcitonin and 100 ml of a 4% aqueous solution of sodium thiosulfate were dropped onto 34 mm-diameter filter paper and freeze-dried to produce a holding material. Upon application, the liner was peeled off and the holding material was attached to the gel side of the test agent to make the iontophoresis electrode device for this example.

EXAMPLE 69

| | |
|---|---|
| Ferric chloride hexahydrate | 4.0 g |
| Agar | 1.0 g |
| Purified water | 95.0 g |
| Total | 100.0 g |

The materials listed above were provided, and after heating the agar to dissolution in the purified water of the test agent, the temperature was lowered to 60° C., and the ferric chloride hexahydrate was added and dissolved therein to prepare a test agent. After packing 1.0 g of the test agent into the cup-shaped packing chamber of an iontophoresis electrode according to Embodiment 3 which had donut-shaped double-sided adhesive tape with an outer diameter of 40 mm and an inner diameter of 30 mm attached to the edge section, the test agent was cooled to solidity. Next, a 44 mm-diameter, 75 µm-thick PET film which had been release-treated was used as a liner and its released side was adhered to the edge section of the backing via double-sided adhesive tape. Separately, 50 µl of a 1% aqueous solution of human insulin was dropped onto 34 mm-diameter filter paper and freeze-dried to produce a holding material. Upon application, the liner was peeled off and the holding material was attached to the gel side of the test agent to make the iontophoresis electrode device for this example.

EXAMPLE 70

| | |
|---|---|
| 30% aqueous solution of hydrogen peroxide | 2.0 g |
| Synthetic aluminum silicate | 1.5 g |
| Agar | 1.0 g |
| Purified water | 95.5 g |
| Total | 100.0 g |

The materials listed above were provided, and after heating the agar to dissolution in the purified water of the materials, the temperature was lowered to 60° C., and the 30% aqueous solution of hydrogen peroxide and synthetic aluminum silicate were added and evenly dispersed therein to prepare a test agent. After packing 1.0 g of the test agent into the packing chamber of an iontophoresis electrode according to Embodiment 5 which had donut-shaped double-sided adhesive tape with an outer diameter of 40 mm and an inner diameter of 30 mm attached to the edge section of the backing, the test agent was cooled to solidity. Next, a 44 mm-diameter, 75 μm-thick PET film which had been release-treated was used as a liner and its released side was adhered to the edge section via double-sided adhesive tape to make the iontophoresis electrode device for this example.

EXAMPLE 71

| | |
|---|---|
| Calcium oxide | 1.0 g |
| Agar | 1.0 g |
| Purified water | 98.0 g |
| Total | 100.0 g |

The materials listed above were provided, and after heating the agar to dissolution in the purified water of the materials, the temperature was lowered to 60° C., and the calcium oxide was added and evenly dispersed therein to prepare a test agent. After packing 1.0 g of the test agent into the packing chamber of an iontophoresis electrode according to Embodiment 1 which had donut-shaped double-sided adhesive tape with an outer diameter of 40 mm and an inner diameter of 30 mm attached to the edge section of the backing, the test agent was cooled to solidity. Next, a 44 mm-diameter, 75 μm-thick PET film which had been release-treated was used as a liner and its released side was adhered to the edge section via double-sided adhesive tape. Separately, 100 ml of a 20% aqueous solution of sodium ascorbate was dropped onto 34 mm-diameter filter paper and freeze-dried to produce a holding material. Upon application, the liner was peeled off and the holding material was attached to the gel side of the test agent to make the iontophoresis electrode device for this example.

Comparative Example 1

An iontophoresis electrode according to Embodiment 9 which had been cut into a 22 mm-diameter disk was affixed via double-sided adhesive tape to one side of a cylindrical cell with a base area of 2.5 cm$^2$ and an electrode distance of 0.5 cm, after which 1.25 ml of a 0.9% aqueous solution of sodium chloride was packed into the cell and a release-treated PET film cut into a 22 mm-diameter disk was affixed to the other side of the cell via double-sided adhesive tape to obtain an iontophoresis electrode device.

Comparative Example 2

An iontophoresis electrode according to Embodiment 2 which had been cut into a 22 mm-diameter disk was affixed via double-sided adhesive tape to one side of a cylindrical cell with a base area of 2.5 cm$^2$ and an electrode distance of 0.5 cm, after which 1.25 ml of a 0.9% aqueous solution of sodium chloride was packed into the cell and a release-treated PET film cut into a 22 mm-diameter disk was affixed to the other side of the cell via double-sided adhesive tape to obtain an iontophoresis electrode device.

Comparative Example 3

An iontophoresis electrode according to Embodiment 2 which had been cut into a 22 mm-diameter disk was affixed via double-sided adhesive tape to one side of a cylindrical cell. with a base area of 2.5 cm$^2$ and an electrode distance of 0.5 cm, after which 1.25 ml of a 2% aqueous solution of ascorbic acid was packed into the cell and a release-treated PET film cut into a 22 mm-diameter disk was affixed to the other side of the cell via double-sided adhesive tape to obtain an iontophoresis electrode device.

Comparative Example 4

An iontophoresis electrode according to Embodiment 2 which had been cut into a 22 mm-diameter disk was affixed via double-sided adhesive tape to one side of a cylindrical cell with a base area of 2.5 cm$^2$ and an electrode distance of 0.5 cm, after which 1.25 ml of an aqueous solution containing 22% ascorbic acid and 0.5% sodium hydroxide was packed into the cell and a release-treated PET film cut into a 22 mm-diameter disk was affixed to the other side of the cell via double-sided adhesive tape to obtain an iontophoresis electrode device.

Comparative Example 5

An iontophoresis electrode according to Embodiment 2 which had been cut into a 22 mm-diameter disk was affixed via double-sided adhesive tape to one side of a cylindrical cell with a base area of 2.5 cm$^2$ and an electrode distance of 0.5 cm, after which 1.25 ml of 0.75% aqueous solution of hydrogen peroxide was packed into the cell and a release-treated PET film cut into a 22 mm-diameter disk was affixed to the other side of the cell via double-sided adhesive tape to obtain an iontophoresis electrode device.

Comparative Example 6

An iontophoresis electrode according to Embodiment 2 which had been cut into a 22 mm-diameter disk was affixed via double-sided adhesive tape to one side of a cylindrical cell with a base area of 2.5 cm$^2$ and an electrode distance of 0.5 cm, after which 1.25 ml of a 0.1 M phosphate buffer solution (pH=7.00) containing 0.75% aqueous solution of hydrogen peroxide was packed into the cell and a release-treated PET film cut into a 22 mm-diameter disk was affixed to the other side of the cell via double-sided adhesive tape to obtain an iontophoresis electrode device.

Comparative Example 7

| | |
|---|---:|
| Tetracaine hydrochloride | 6.0 g |
| Agar | 1.0 g |
| Purified water | 93.0 g |
| Total | 100.0 g |

The materials listed above were provided, the agar was heated to dissolution in half the amount of purified water of the materials, and upon reaching 60° C. a solution of the tetracaine hydrochloride which had been previously dissolved and heated to 60° C. in the remaining purified water was added thereto to prepare a test agent. After packing 1.0 g of the test agent into the packing chamber of an iontophoresis electrode according to Embodiment 1 which had donut-shaped double-sided adhesive tape with an outer diameter of 40 mm and an inner diameter of 30 mm attached to the edge of the backing the test agent was cooled to solidity. Next, a 44 mm-diameter, 75 μm-thick PET film which had been release-treated was used as a liner and its released side was adhered to the edge section of the backing via the double-sided adhesive tape, to obtain an iontophoresis electrode device.

Comparative Example 8

| | |
|---|---:|
| Calcium silicate | 1.5 g |
| Gelan gum | 1.0 g |
| Purified water | 97.5 g |
| Total | 100.0 g |

The materials listed above were provided, and after heating the agar to dissolution in the purified water of the materials, the temperature was lowered to 70° C., the calcium silicate was added and the mixture was uniformly dispersed to prepare a test agent. After packing 1.0 g of the test agent into the packing chamber of an iontophoresis electrode according to Embodiment 1 which had donut-shaped double-sided adhesive tape with an outer diameter of 40 mm and an inner diameter of 30 mm attached to the edge section of the backing, it was cooled to solidity. Next, a 44 mm-diameter, 75 μm-thick PET film which had been release-treated was used as a liner and its released side was adhered to the edge section via double-sided adhesive tape. Separately, 10 μl of a 0.04% aqueous solution of salmon calcitonin was dropped onto 34 mm-diameter filter paper and freeze-dried to produce a holding material. Upon application, the holding material was attached to the gel side of the test agent to make the iontophoresis electrode device.

Comparative Example 9

| | |
|---|---:|
| Sodium hydroxide | 1.0 g |
| Gelan gum | 1.0 g |
| Purified water | 98.0 g |
| Total | 100.0 g |

The materials listed above were provided, and after heating the agar to dissolution in the purified water of the materials, the temperature was lowered to 70° C., the sodium hydroxide was added and the mixture was uniformly dispersed to prepare a test agent. After packing 1.0 g of the test agent into the packing chamber of an iontophoresis electrode according to Embodiment 1 which had donut-shaped double-sided adhesive tape with an outer diameter of 40 mm and an inner diameter of 30 mm attached to the edge section of the backing, it was cooled to solidity. Next, a 44 mm-diameter, 75 μm-thick PET film which had been release-treated was used as a liner and its released side was adhered to the edge section via double-sided adhesive tape. Separately, 10 μl of a 0.04% aqueous solution of salmon calcitonin and 100 ml of a 4% aqueous solution of sodium thiosulfate were dropped onto 34 mm-diameter filter paper and freeze-dried to produce a holding material. Upon application, the holding material was attached to the gel side of the test agent to make an iontophoresis electrode device.

Comparative Example 10

| | |
|---|---:|
| Calcium chloride | 0.1 g |
| Gelan gum | 1.0 g |
| Purified water | 98.9 g |
| Total | 100.0 g |

The materials listed above were provided, and after heating the agar to dissolution in the purified water of the materials, the temperature was lowered to 70° C. and the calcium chloride was added and dissolved to prepare a test agent. After packing 1.0 g of the test agent into the packing chamber of an iontophoresis electrode according to Embodiment 10 which had donut-shaped double-sided adhesive tape with an outer diameter of 40 mm and an inner diameter of 30 mm attached to the edge section of the backing, it was cooled to solidity. Next, a 44 mm-diameter, 75 μm-thick PET film which had been release-treated was used as a liner and its released side was adhered to the edge section via double-sided adhesive tape. Separately, 10 μl of a 0.04% aqueous solution of salmon calcitonin was dropped onto 34 mm-diameter filter paper and freeze-dried to produce a holding material. Upon application, the holding material was attached to the gel side of the test agent to make an iontophoresis electrode device.

Comparative Example 11

| | |
|---|---|
| Calcium chloride | 3.0 g |
| Gelan gum | 1.0 g |
| Purified water | 96.0 g |
| Total | 100.0 g |

The materials listed above were provided, and after heating the agar to dissolution in the purified water of the materials, the temperature was lowered to 70° C., and the calcium chloride was added and dissolved to prepare a test agent. After packing 1.0 g of the test agent into the packing chamber of an iontophoresis electrode according to Embodiment 10 which had donut-shaped double-sided adhesive tape with an outer diameter of 40 mm and an inner diameter of 30 mm attached to the edge section of the backing, it was cooled to solidity. Next, a 44 mm-diameter, 75 µm-thick PET film which had been release-treated was used as a liner and its released side was adhered to the edge section via double-sided adhesive tape. Separately, 10 µl of a 0.04% aqueous solution of salmon calcitonin was dropped onto 34 mm-diameter filter paper and freeze-dried to produce a holding material. Upon application, the holding material was attached to the gel side of the test agent to make an iontophoresis electrode device.

Comparative Example 12

| | |
|---|---|
| Sodium chloride | 0.2 g |
| Agar | 1.0 g |
| Purified water | 98.8 g |
| Total | 100.0 g |

The materials listed above were provided, and after heating the agar and sodium chloride to dissolution in the purified water of the materials, the temperature was lowered to 60° C. to prepare a test agent. After packing 1.0 g of the test agent into the packing chamber of an iontophoresis electrode according to Embodiment 3 which had donut-shaped double-sided adhesive tape with an outer diameter of 40 mm and an inner diameter of 30 mm attached to the edge section, it was cooled to solidity. Next, a 44 mm-diameter, 75 µm-thick PET film which had been release-treated was used as a liner and its released side was adhered to the edge section via double-sided adhesive tape. Separately, 50 µl of a 1% aqueous solution of human insulin was dropped onto 34 mm-diameter filter paper and freeze-dried to produce a holding material. Upon application, the holding material was attached to the gel side of the test agent to make an iontophoresis electrode device. Comparative Example 13

| | |
|---|---|
| Sodium chloride | 3.0 g |
| Agar | 1.0 g |
| Purified water | 96.0 g |
| Total | 100.0 g |

The materials listed above were provided, and after heating the agar and sodium chloride to dissolution in the purified water of the materials, the temperature was lowered to 60° C. to prepare a test agent. After packing 1.0 g of the test agent into the packing chamber of an iontophoresis electrode according to Embodiment 8 which had donut-shaped double-sided adhesive tape with an outer diameter of 40 mm and an inner diameter of 30 mm attached to the edge section, it was cooled to solidity. Next, a 44 mm-diameter, 75 µm-thick PET film which had been release-treated was used as a liner and its released side was adhered to the edge section via double-sided adhesive tape to make an iontophoresis electrode device. Comparative Example 14

| | |
|---|---|
| Sodium chloride | 3.0 g |
| Agar | 1.0 g |
| Purified water | 96.0 g |
| Total | 100.0 g |

The materials listed above were provided, and after heating the agar and sodium chloride to dissolution in the purified water of the materials, the temperature was lowered to 60° C. to prepare a test agent. After packing 1.0 g of the test agent into the packing chamber of an iontophoresis electrode according to Embodiment 10 which had donut-shaped double-sided adhesive tape with an outer diameter of 40 mm and an inner diameter of 30 mm attached to the edge section, it was cooled to solidity. Next, a 44 mm-diameter, 75 µm-thick PET film which had been release-treated was used as a liner and its released side was adhered to the edge section via double-sided adhesive tape to make an iontophoresis electrode device.

Experimental Examples 1–23

Iontophoresis electrode devices according to Examples 1 through 20 and Comparative Examples 1 and 2 were provided with iontophoresis electrodes according to Embodiments 7 or 9 cut. to a disk shape with a diameter of 22 mm, in the combinations listed in Tables 9 and 10, and after peeling off the liner of each iontophoresis electrode device, it was attached to the iontophoresis electrode, a pulse current of 1 mA was applied to each electrode terminal, and the transport current values and voltage values were measured after 1, 2 and 3 hours. The results of the measurement are shown in Tables 9 and 10.

Figure 5:
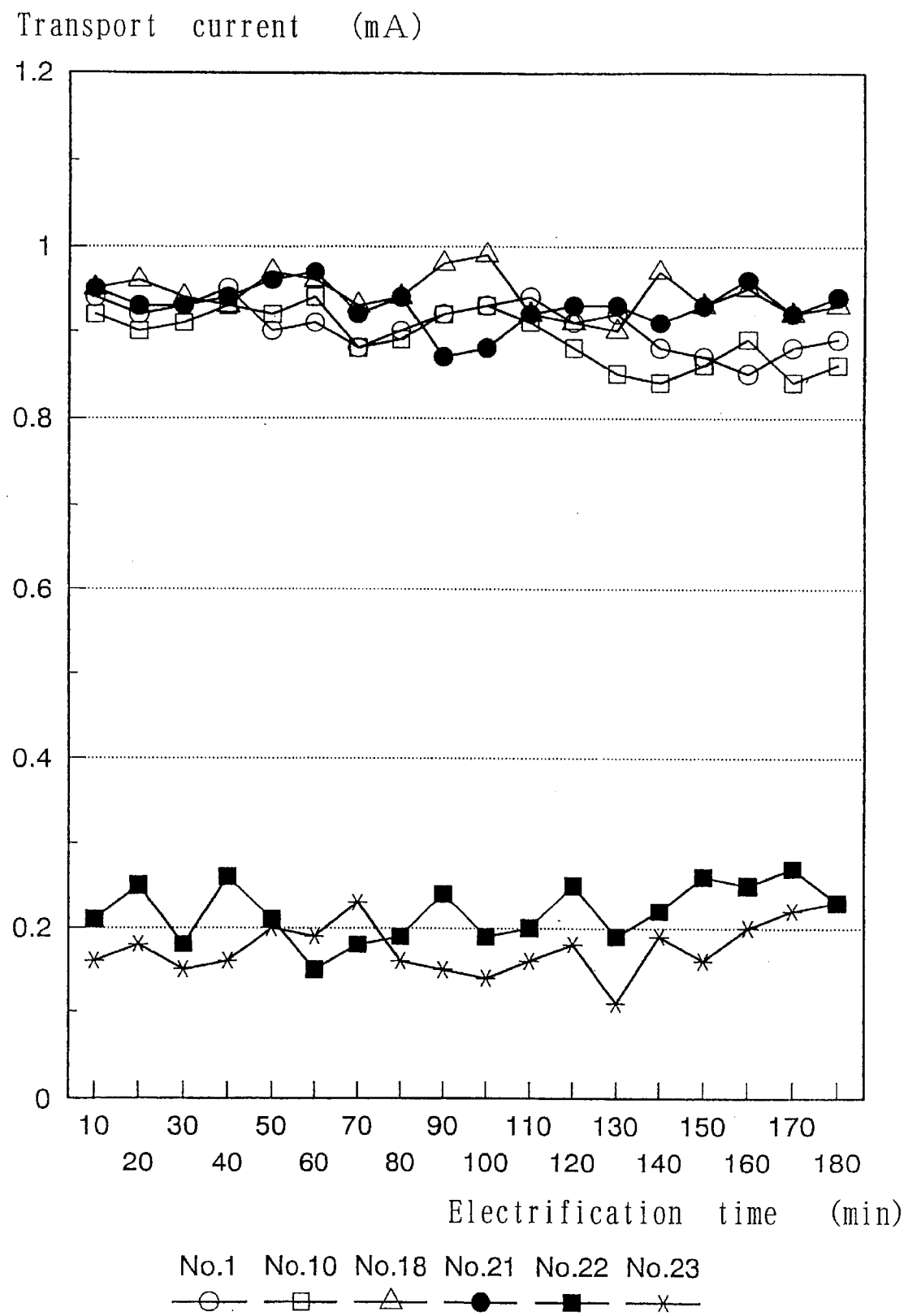
FIG. 5 is a graph showing the change in transport current with time.
Figure 6:
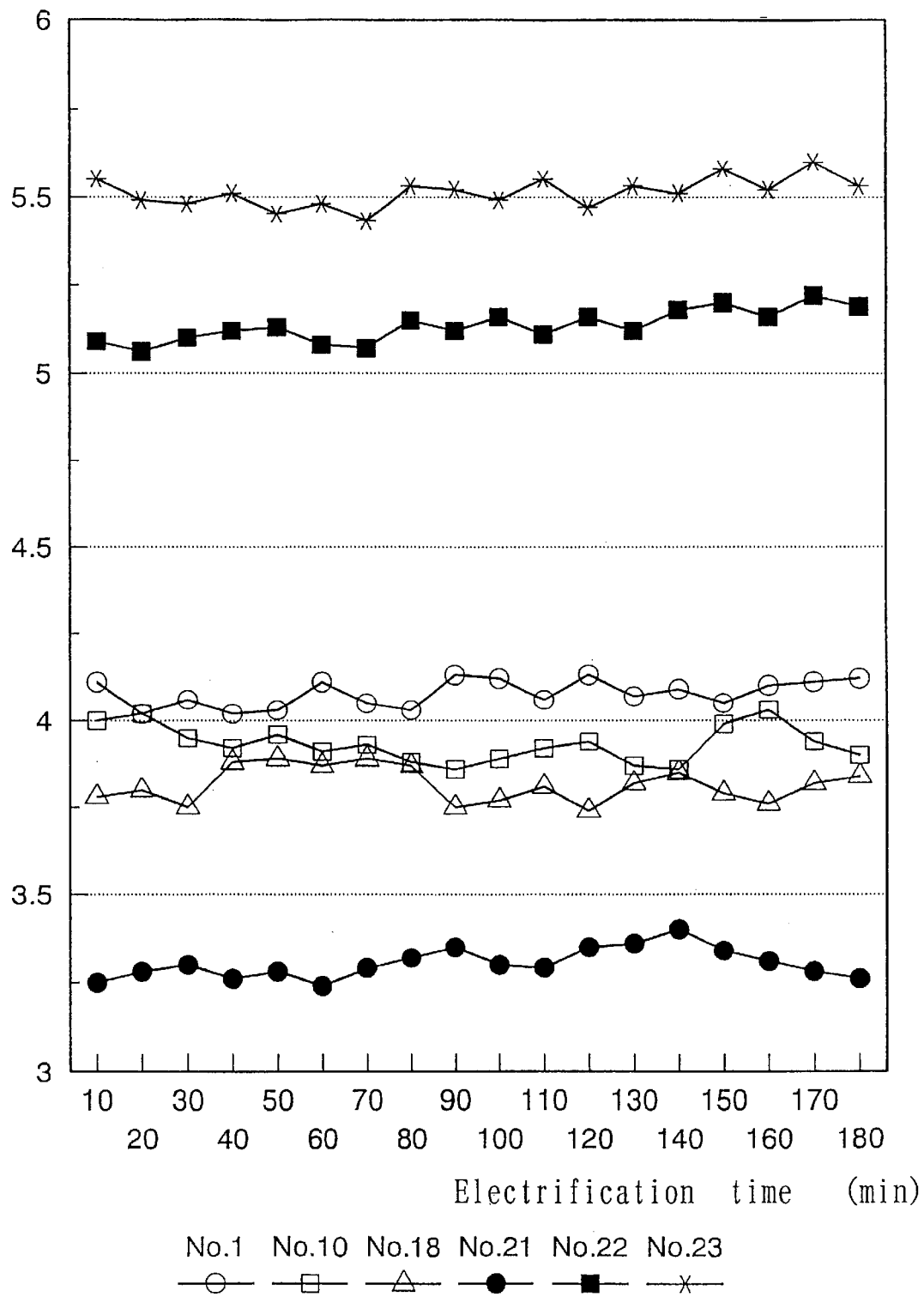
FIG. 6 is a graph showing the change in voltage with time.

Also, FIG. 5 shows the change in transport current for Experimental Examples NO.1, 10, 18, 21, 22 and 23, while FIG. 6 shows their voltage changes. As clearly shown by Tables 9 and 10 and FIG. 5, Experimental Examples NO.1 to NO.20 according to the examples which were combinations of inert electrodes and depolarizers had no reduction in transport current at either the anode or cathode, in contrast to Experimental Example NO.21 as the comparison. Also, as clearly shown by Tables 9 and 10 and FIG. 6, Experimental Examples NO.1 and NO.4 to 20 according to the examples had only slight increase in voltage due to carbon resistance. Because the iontophoresis electrode device and iontophoresis electrode are connected in series through the human body, the voltage increase has absolutely no effect on the voltage applied to the body. Experimental Examples NO.22 and 23 as the comparative examples, which were combinations of electrolyte solutions and inert electrodes with no depolarizer added, produced a decrease in transport current by pilarization, and the voltages were also higher. Also, no difference was found in the transport current values and voltages of Experimental Example NO.11 which employed ascorbic acid as the depolarizer and Experimental Example NO.17 which employed its salt sodium ascorbate, thus confirming that the depolarizing effect is not altered even when a salt is used as the depolarizer. Although considerable foaming was observed on the electrode surface of the anode of Experimental Example NO.22 and the electrode surface of the cathode of Experimental Example NO.23 which employed iontophoresis electrode devices as comparative examples, it was not observed on any of the other electrodes.

Experimental Examples 24–46

Iontophoresis electrode devices according to Examples 21 through 41 and Comparative Examples 3 and 4 were provided with iontophoresis electrodes according to Embodiment 7, and the changes in pH values during electrification were determined using the combinations listed in Table 11. The iontophoresis electrode of Embodiment 7 cut into a 22 mm-diameter disk was attached to one side of a cylindrical cell with an inner diameter of 17.8 mm and an electrode distance of 5 mm via double-sided adhesive tape, while on the other side of the cell, the liner was peeled off and each of the iontophoresis electrode devices of Examples 21 through 41 and Comparative Examples 3 and 4 to which filter paper cut into a 22 mm-diameter disk had been affixed was attached thereto from the filter paper side and anchored with clips to fabricate samples. The initial pH values on the filter paper surface and the pH values were measured at 3 hours after applying a 1 mA pulse current to each electrode terminal. The results are shown in Table 11.

As seen from Table 11, the initial pH values and values after 3 hours of electrification in Experimental Examples NO.24 to NO.44 which employed iontophoresis electrode devices according to the examples with poorly soluble pH regulators added were all controlled within a range from 3 to 11. In contrast, strong acidity was exhibited in Experimental Example NO.45 which employed an iontophoresis electrode device according to a comparative example with no pH regulator added, and strong acidity was also exhibited after 3 hours of electrification even with further addition of sodium hydroxide for a higher initial pH value in Experimental Example NO.46.

Experimental Examples 47–68

Iontophoresis electrode devices according to Examples 42 through 61 and Comparative Examples 5 and 6 were provided with iontophoresis electrodes according to Embodiment 9, in the combinations listed in Table 12, and the changes in pH values during electrification were confirmed.

The iontophoresis electrode of Embodiment 9 which had been cut into a disk of 22 mm diameter was fixed to one side of each cylindrical cell with an inner diameter of 17.8 mm and an electrode distance of 5 mm using double-sided adhesive tape, while on the other side of the cell, the PET film was peeled off and each of the iontophoresis electrode devices of Examples 42 to 61 and Comparative Examples 5 and 6 to which filter paper cut into a 22 mm-diameter disk had been affixed was attached thereto from the filter paper side and anchored with clips to fabricate samples. The initial pH values on the filter paper surface and the pH values were measured at 3 hours after applying a 1 mA pulse current to each electrode terminal. The results are shown in Table 12.

As seen from Table 12, the pH values in Experimental Examples NO.47 to NO.66 which employed iontophoresis electrode devices according to the examples with poorly soluble pH regulators added were all controlled within a range from 4 to 12. In contrast, strong alkalinity was exhibited in Experimental Example NO.67 which employed an iontophoresis electrode device according to a comparative example with no pH regulator added, and strong alkalinity was also exhibited after 3 hours of electrification even in Experimental Example NO.68 in which a phosphate buffer solution was further added to exhibit a buffering effect, demonstrating that it could not withstand practical use for over 3 hours from a safety standpoint.

Experimental Examples 69–75

Iontophoresis electrode devices according to Examples 6.2 through 67 and 70 and Comparative Example 7 were provided in the combinations listed in Table 13, and the local anesthetic effect indexes (%) after electrification were confirmed. The test was carried out with 5 healthy male adults using the Experimental Examples in Table 13, with the tetracaine local anesthetic effect determined as an index for drug penetration, whereby after each electrification time the site of application was lightly pricked with a syringe and evaluation was made based on the scale listed in Table 14. The symbol "+" in the evaluation indicates that electrification was terminated.

As clearly shown in Table 13, Experimental Examples NO.69 to NO.74 which employed iontophoresis electrode device; according to the examples comprising combinations of inert electrodes and depolarizers all exhibited a notable effect index within 30 minutes, while Experimental Example NO.75, which employed an iontophoresis electrode device according to a comparative example comprising a combination of an inert electrode with an electrolyte solution containing no depolarizer, failed to exhibit an adequate effect index even after 120 minutes of electrification. Also, no difference was found in the effect depending on the type of inert electrode used, as seen by the results for Experimental Examples NO.70 to NO.72 according to the examples. Incidentally, although Experimental Example NO.73 had no poorly soluble pH regulator added, no irritation was observed with short-term application.

Experimental Examples 76–80

Figure 7:
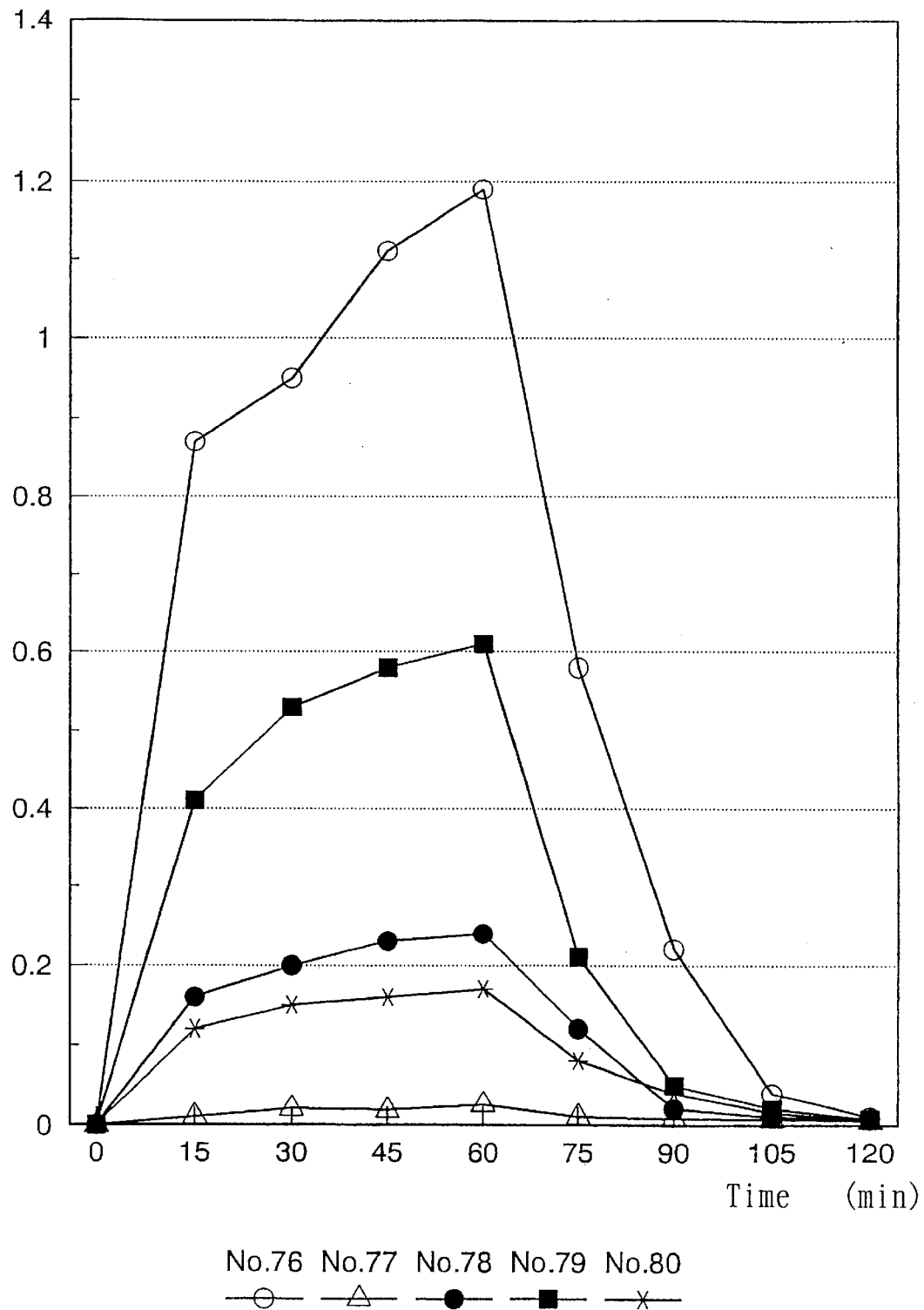
FIG. 7 is a graph showing the change in rat serum levels of salmon calcitonin with time.

Iontophoresis electrode devices according to Examples 68 and 70 and Comparative Examples 8 through 11 and 14 were provided, in the combinations listed in Table 15, and a blood kinetics test for salmon calcitonin was conducted. The test was a blood kinetics test in which salmon calcitonin was administered to rats as a cationic model drug using the experimental examples listed in Table 15. The results are shown in Table 15 and FIG. 7. FIG. 7 shows the average values for 4 cases each.

As clearly seen from FIG. 7 and Table 15, Experimental Example NO.76 which employed an iontophoresis electrode device according to the examples comprising a combination of an inert electrode, a depolarizer and a poorly soluble pH regulator had a greater maximum serum drug concentration (Cmax) and serum drug concentration area-under-the-curve (AUC) than Experimental Example NO.77 which employed an iontophoresis, electrode device according to a comparative example which was a combination of an inert electrode with an electrolyte solution containing no depolarizer, NO.78 comprising a combination of an inert electrode with a readily soluble pH regulator and a depolarizer, NO.79 in which silver and a small amount of calcium chloride were combined for the reactive electrode, and NO.80 in which silver and a small amount of calcium chloride were combined for the reactive electrode. In addition, as shown in Table 15, NO.78 wherein a readily soluble substance was used as the pH regulator had an inadequate pH regulating effect, and flare was observed. A reduction in drug permeability was also found due to an abundance of competing ions. NO.79 with the combination of a reactive electrode resulted in blackening of the skin with silver chloride, because of the low amount of calcium chloride, suggesting penetration of silver ions into the skin. No blackening of the skin was found with NO.80 in which more calcium chloride was added, but a reduction in drug permeability was confirmed. No skin irritation or blackening was found with NO.76 which comprised a combination of an inert electrode, a depolarizer and a poorly soluble pH regulator, and a high drug permeability was confirmed.

Experimental Examples 81–82

Figure 8:
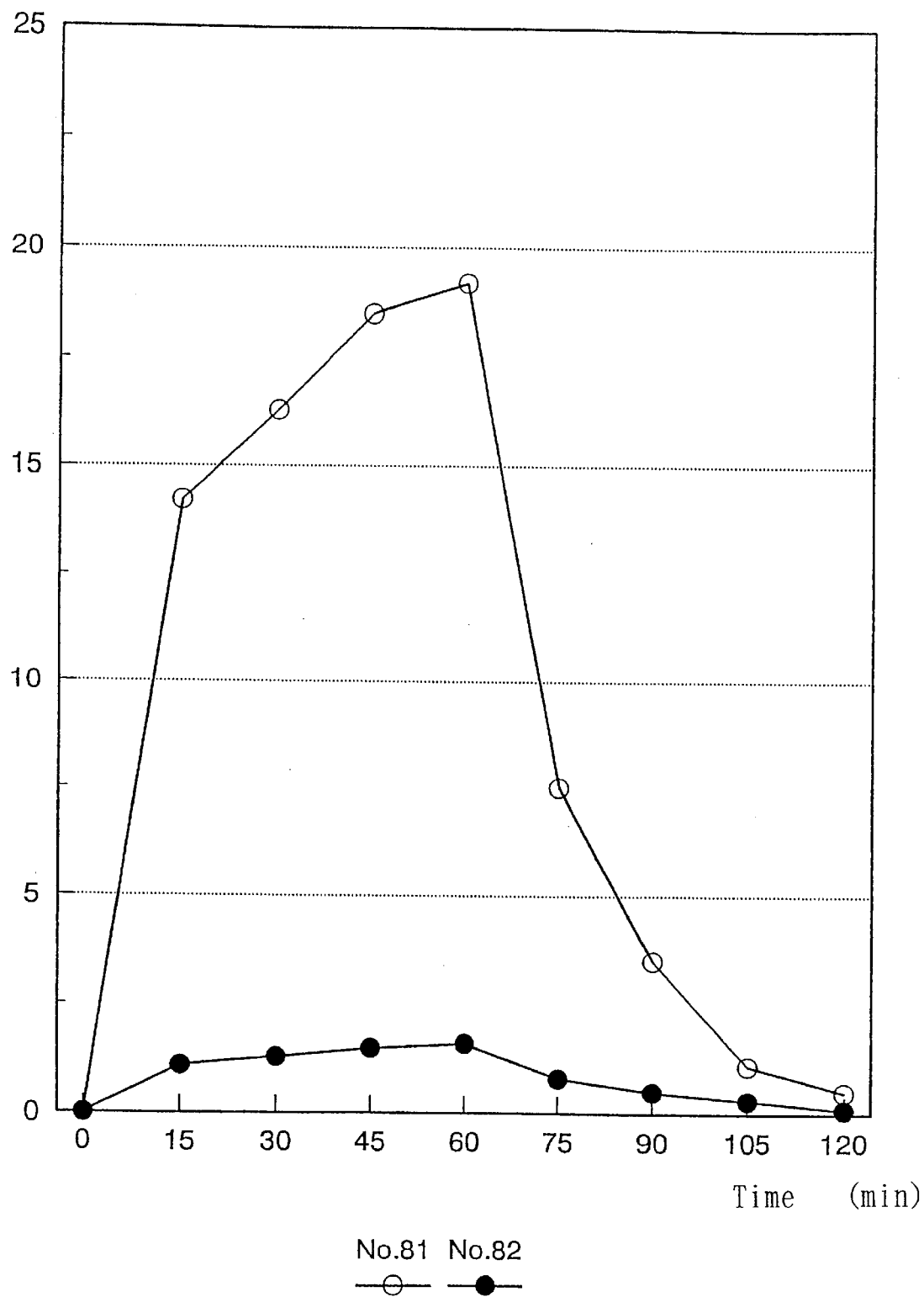
FIG. 8 is a graph showing the change in rat serum levels of human insulin with time.

Iontophoresis electrode devices according to Examples 69 and 71 and Comparative Examples 12 and 14 were provided, in the combinations listed in Table 16, and a blood kinetics test for human insulin was conducted. The test was a blood kinetics test in which human insulin was administered to rats as an anionic model drug using the experimental examples listed in Table 16. The results are shown in Table 16 and FIG. 8. FIG. 8 shows the average values for 4 cases each.

As clearly seen from Table 16 and FIG. 8, Experimental Example NO.81 which employed an iontophoresis electrode device according to the examples comprising a combination of an inert electrode, a depolarizer and a poorly soluble pH regulator had a Cmax and AUC at least 10 times greater than Experimental Example NO.82 which employed an iontophoresis electrode device according to a comparative example which was a combination of an inert electrode with an electrolyte solution containing no poorly soluble pH regulator. Also, as shown in Table 16, sample NO.82 according to the comparative example in which no poorly soluble pH regulator was added resulted in observed skin irritation on the cathode-applied surface, while no skin irritation was found with Experimental Example NO.81 according to the examples in which a poorly soluble pH regulator was added.

Industrial Applicability

As explained above, the present invention realizes iontophoresis electrode devices exhibiting the following excellent effects.

(1) Because inert electrodes are used as the electrodes, there is no entrance of metal ions from the electrodes into the body, resulting in notably improved safety.

(2) Reuse is possible by simply packing the drugs, and production at low cost is achievable when carbon is used for the inert electrodes, thus allowing better mass production.

(3) Because combinations of inert electrodes and depolarizers are used, polarization can be markedly reduced, to allow an improved transport current efficiency.

(4) By including poorly soluble pH regulators in the electrolyte solvents, it is possible to prevent skin injury due to pH changes during prolonged application.

(5) They can be used without interfering with long-term drug penetration.

$SO_3^{2-} + H_2O \rightarrow SO_4^{2-} + 2e^-$ Chemical equation 1

$2HSCH_2COO^- \rightarrow {}^-OOCH_2S-SCH_2COO^{31-} + 2H^+ + 2e^-$ Chemical equation 2

$3I^- \rightarrow I_3^- + 2e^-$ Chemical equation 3

$Fe^{3+} + e^- \rightarrow Fe^{2-}$ Chemical equation 4

$H_2O_2 + 2e^- \rightarrow 2OH^-$ Chemical equation 5

$CaO + 2H^+ \rightarrow Ca^{2+} + H_2O$ Chemical equation 6

$Ph(CO)_2 + 2OH^- \rightarrow Ph(COO^-)_2 + H_2O$ Chemical equation 7

$Al_2O_3 \cdot MgO \cdot 2SiO_2 \cdot xH_2O + 8H^+ \rightarrow 2Al^{3+} + Mg^{2+} + 2SiO_2 + (x+4)H_2O$ Chemical equation 8

$Al(OH)_3 \cdot xH_2O + OH^- \rightarrow AlO_2^- + (x+2)H_2O$ Chemical equation 9

TABLE 1

| Embodiments | Depolarizer | Amount of regulator added | Purified water | Total amount |
|---|---|---|---|---|
| Embodiment 11 | ascorbic acid | 2.0 g | q.s. | 100 ml |
| Embodiment 12 | erythorbic acid | 2.0 g | q.s. | 100 ml |
| Embodiment 13 | cysteine | 2.7 g | q.s. | 100 ml |
| Embodiment 14 | acetylcysteine | 3.7 g | q.s. | 100 ml |
| Embodiment 15 | thioglycolic acid | 2.1 g | q.s. | 100 ml |
| Embodiment 16 | sodium thiomalate | 4.4 g | q.s. | 100 ml |
| Embodiment 17 | sodium ascorbate | 2.2 g | q.s. | 100 ml |
| Embodiment 18 | sodium sulfite | 1.4 g | q.s. | 100 ml |
| Embodiment 19 | sodium hydrogen sulfite | 1.2 g | q.s. | 100 ml |
| Embodiment 20 | sodium thiosulfate | 0.7 g | q.s. | 100 ml |
| Embodiment 21 | sodium pyrosulfite | 1.1 g | q.s. | 100 ml |
| Embodiment 22 | potassium pyrosulfite | 1.2 g | q.s. | 100 ml |
| Embodiment 23 | sodium nitrite | 0.8 g | q.s. | 100 ml |
| Embodiment 24 | α-thioglycerine | 4.8 g | q.s. | 100 ml |
| Embodiment 25 | potassium iodide | 3.7 g | q.s. | 100 ml |
| Embodiment 26 | ferric chloride hexahydrate | 6.0 g | q.s. | 100 ml |
| Embodiment 27 | copper sulfate pentahydrate | 5.6 g | q.s. | 100 ml |
| Embodiment 28 | 30% aqueous solution of hydrogen peroxide | 2.5 ml | q.s. | 100 ml |

Embodiment 28 contained 0.45% sodium chloride

TABLE 2

| Embodiments | Anode pH regulator | Amount of regulator added | Depolarizer | Amount of depolarizer added | Purified water | Total amount |
|---|---|---|---|---|---|---|
| Embodiment 29 | calcium oxide | 1.2 g | ascorbic acid | 2.0 g | q.s. | 100 ml |
| Embodiment 30 | magnesium oxide | 0.9 g | ascorbic acid | 2.0 g | q.s. | 100 ml |
| Embodiment 31 | calcium hydroxide | 1.6 g | erythorbic acid | 2.0 g | q.s. | 100 ml |
| Embodiment 32 | magnesium hydroxide | 1.3 g | erythorbic acid | 2.0 g | q.s. | 100 ml |
| Embodiment 33 | hydroxyapatite | 5.0 g | ascorbic acid | 2.0 g | q.s. | 100 ml |
| Embodiment 34 | γ-alumina | 0.8 g | ascorbic acid | 2.0 g | q.s. | 100 ml |
| Embodiment 35 | aluminum hydroxide | 1.2 g | thioglycolic acid | 2.1 g | q.s. | 100 ml |
| Embodiment 36 | dry aluminum hydroxide gel | 0.8 g | thioglycolic acid | 2.1 g | q.s. | 100 ml |
| Embodiment 37 | magnesium aluminum hydroxide | 2.0 g | sodium sulfite | 1.4 g | q.s. | 100 ml |
| Embodiment 38 | aluminum glycinate | 2.0 g | sodium sulfite | 1.4 g | q.s. | 100 ml |
| Embodiment 39 | synthetic hydrotalcite | 1.5 g | sodium thiosulfate | 0.7 g | q.s. | 100 ml |

TABLE 3

| Embodiments | Anode pH regulator | Amount of regulator added | Depolarizer | Amount of depolarizer added | Purified water | Total amount |
|---|---|---|---|---|---|---|
| Embodiment 40 | zeolite | 3.0 g | sodium thiosulfate | 0.7 g | q.s. | 100 ml |
| Embodiment 41 | synthetic aluminum silicate | 2.5 g | potassium pyrosulfite | 3.7 g | q.s. | 100 ml |
| Embodiment 42 | natural aluminum silicate | 2.5 g | potassium pyrosulfite | 1.2 g | q.s. | 100 ml |
| Embodiment 43 | magnesium aluminosilicate | 1.1 g | sodium nitrite | 0.8 g | q.s. | 100 ml |
| Embodiment 44 | magnesium aluminometasilicate | 1.5 g | α-thioglycerine | 2.4 g | q.s. | 100 ml |
| Embodiment 45 | bismuth magnesium aluminosilicate | 1.2 g | sodium pyrosulfite | 1.1 g | q.s. | 100 ml |
| Embodiment 46 | magaldrate | 1.6 g | sodium ascorbate | 2.2 g | q.s. | 100 ml |
| Embodiment 47 | calcium silicate | 2.6 g | cysteine | 2.7 g | q.s. | 100 ml |
| Embodiment 48 | magnesium silicate | 2.9 g | acetylcysteine | 3.7 g | q.s. | 100 ml |
| Embodiment 49 | zinc oxide | 1.8 g | sodium thiomalate | 4.4 g | q.s. | 100 ml |

TABLE 4

| Embodiments | Cathode pH regulator | Amount of regulator added | Depolarizer | Amount of depolarizer added | Purified water | Total amount |
|---|---|---|---|---|---|---|
| Embodiment 50 | silica gel | 1.4 g | 30% aqueous solution of hydrogen peroxide | 2.5 ml | q.s. | 100 ml |
| Embodiment 51 | light silicic anhydride | 1.4 g | 30% aqueous solution of hydrogen peroxide | 2.5 ml | q.s. | 100 ml |
| Embodiment 52 | phthalic anhydride | 3.3 g | 30% aqueous solution of hydrogen peroxide | 2.5 ml | q.s. | 100 ml |
| Embodiment 53 | isobutylene-maleic anhydride copolymer | 3.4 g | 30% aqueous solution of hydrogen peroxide | 2.5 ml | q.s. | 100 ml |
| Embodiment 54 | γ-alumina | 2.3 g | 30% aqueous solution of hydrogen peroxide | 2.5 ml | q.s. | 100 ml |
| Embodiment 55 | aluminum hydroxide | 3.5 g | 30% aqueous solution of hydrogen peroxide | 2.5 ml | q.s. | 100 ml |
| Embodiment 56 | dry aluminum hydroxide gel | 2.3 g | 30% aqueous solution of hydrogen peroxide | 2.5 ml | q.s. | 100 ml |
| Embodiment 57 | magnesium aluminum hydroxide | 4.0 g | 30% aqueous solution of hydrogen peroxide | 2.5 ml | q.s. | 100 ml |
| Embodiment 58 | aluminum glycinate | 6.0 g | 30% aqueous solution of hydrogen peroxide | 2.5 ml | q.s. | 100 ml |
| Embodiment 59 | synthetic hydrotalcite | 6.8 g | 30% aqueous solution of hydrogen peroxide | 2.5 ml | q.s. | 100 ml |

TABLE 5

| Embodiments | Anode pH regulator | Amount of regulator added | Depolarizer | Amount of depolarizer added | Purified water | Total amount |
|---|---|---|---|---|---|---|
| Embodiment 60 | zeolite | 2.5 g | 30% aqueous solution of hydrogen peroxide | 2.5 ml | q.s. | 100 ml |

TABLE 5-continued

| Embodiments | Anode pH regulator | Amount of regulator added | Depolarizer | Amount of depolarizer added | Purified water | Total amount |
|---|---|---|---|---|---|---|
| Embodiment 61 | synthetic aluminum silicate | 1.6 g | 30% aqueous solution of hydrogen peroxide | 2.5 ml | q.s. | 100 ml |
| Embodiment 62 | natural aluminum silicate | 1.4 g | 30% aqueous solution of hydrogen peroxide | 2.5 ml | q.s. | 100 ml |
| Embodiment 63 | magnesium aluminosilicate | 2.7 g | 30% aqueous solution of hydrogen peroxide | 2.5 ml | q.s. | 100 ml |
| Embodiment 64 | magnesium aluminometasilicate | 2.0 g | 30% aqueous solution of hydrogen peroxide | 2.5 ml | q.s. | 100 ml |
| Embodiment 65 | bismuth magnesium aluminosilicate | 3.0 g | 30% aqueous solution of hydrogen peroxide | 2.5 ml | q.s. | 100 ml |
| Embodiment 66 | magaldrate | 9.8 g | 30% aqueous solution of hydrogen peroxide | 2.5 ml | q.s. | 100 ml |
| Embodiment 67 | calcium silicate | 2.6 g | 30% aqueous solution of hydrogen peroxide | 2.5 ml | q.s. | 100 ml |
| Embodiment 68 | magnesium silicate | 2.0 g | 30% aqueous solution of hydrogen peroxide | 2.5 ml | q.s. | 100 ml |
| Embodiment 69 | zinc oxide | 1.8 g | 30% aqueous solution of hydrogen peroxide | 2.5 ml | q.s. | 100 ml |

TABLE 6

| Examples | Electrolyte solution | Iontophoresis electrode |
|---|---|---|
| Example 1 | Embodiment 11 | Embodiment 2 |
| Example 2 | Embodiment 11 | Embodiment 4 |
| Example 3 | Embodiment 11 | Embodiment 6 |
| Example 4 | Embodiment 12 | Embodiment 2 |
| Example 5 | Embodiment 13 | Embodiment 2 |
| Example 6 | Embodiment 14 | Embodiment 2 |
| Example 7 | Embodiment 15 | Embodiment 2 |
| Example 8 | Embodiment 16 | Embodiment 2 |
| Example 9 | Embodiment 17 | Embodiment 2 |
| Example 10 | Embodiment 18 | Embodiment 2 |
| Example 11 | Embodiment 19 | Embodiment 2 |
| Example 12 | Embodiment 20 | Embodiment 2 |
| Example 13 | Embodiment 21 | Embodiment 2 |
| Example 14 | Embodiment 22 | Embodiment 2 |
| Example 15 | Embodiment 23 | Embodiment 2 |
| Example 16 | Embodiment 24 | Embodiment 2 |
| Example 17 | Embodiment 25 | Embodiment 2 |
| Example 18 | Embodiment 26 | Embodiment 2 |
| Example 19 | Embodiment 27 | Embodiment 2 |
| Example 20 | Embodiment 28 | Embodiment 2 |

TABLE 7

| Examples | Electrolyte solution | Iontophoresis electrode |
|---|---|---|
| Example 21 | Embodiment 29 | Embodiment 2 |
| Example 22 | Embodiment 30 | Embodiment 2 |
| Example 23 | Embodiment 31 | Embodiment 2 |
| Example 24 | Embodiment 32 | Embodiment 2 |
| Example 25 | Embodiment 33 | Embodiment 2 |
| Example 26 | Embodiment 34 | Embodiment 2 |
| Example 27 | Embodiment 35 | Embodiment 2 |
| Example 28 | Embodiment 36 | Embodiment 2 |
| Example 29 | Embodiment 37 | Embodiment 2 |
| Example 30 | Embodiment 38 | Embodiment 2 |
| Example 31 | Embodiment 39 | Embodiment 2 |
| Example 32 | Embodiment 40 | Embodiment 2 |
| Example 33 | Embodiment 41 | Embodiment 2 |
| Example 34 | Embodiment 42 | Embodiment 2 |
| Example 35 | Embodiment 43 | Embodiment 2 |
| Example 36 | Embodiment 44 | Embodiment 2 |
| Example 37 | Embodiment 45 | Embodiment 2 |
| Example 38 | Embodiment 46 | Embodiment 2 |
| Example 39 | Embodiment 47 | Embodiment 2 |
| Example 40 | Embodiment 48 | Embodiment 2 |

TABLE 8

| Examples | Electrolyte solution | Iontophoresis electrode |
|---|---|---|
| Example 41 | Embodiment 49 | Embodiment 2 |
| Example 42 | Embodiment 50 | Embodiment 2 |
| Example 43 | Embodiment 51 | Embodiment 2 |
| Example 44 | Embodiment 52 | Embodiment 2 |
| Example 45 | Embodiment 53 | Embodiment 2 |
| Example 46 | Embodiment 54 | Embodiment 2 |
| Example 47 | Embodiment 55 | Embodiment 2 |
| Example 48 | Embodiment 56 | Embodiment 2 |
| Example 49 | Embodiment 57 | Embodiment 2 |
| Example 50 | Embodiment 58 | Embodiment 2 |
| Example 51 | Embodiment 59 | Embodiment 2 |
| Example 52 | Embodiment 60 | Embodiment 2 |
| Example 53 | Embodiment 61 | Embodiment 2 |
| Example 54 | Embodiment 62 | Embodiment 2 |
| Example 55 | Embodiment 63 | Embodiment 2 |
| Example 56 | Embodiment 64 | Embodiment 2 |
| Example 57 | Embodiment 65 | Embodiment 2 |
| Example 58 | Embodiment 66 | Embodiment 2 |
| Example 59 | Embodiment 67 | Embodiment 2 |
| Example 60 | Embodiment 68 | Embodiment 2 |
| Example 61 | Embodiment 69 | Embodiment 2 |

TABLE 9

| Experimental Example | Anode | Cathode | 1 Hour electrification | | 2 Hours electrification | | 3 Hours electrification | |
|---|---|---|---|---|---|---|---|---|
| | | | Transport Current | Voltage (V) | Transport Current | Voltage (V) | Transport Current | Voltage (V) |
| NO. 1 | Example 1 | Embodiment 7 | 0.91 | 4.11 | 0.91 | 4.13 | 0.89 | 4.12 |
| NO. 2 | Example 2 | Embodiment 7 | 0.92 | 3.25 | 0.93 | 3.29 | 0.91 | 3.25 |
| NO. 3 | Example 3 | Embodiment 7 | 0.89 | 3.27 | 0.90 | 3.30 | 0.90 | 3.29 |
| NO. 4 | Example 4 | Embodiment 7 | 0.91 | 4.12 | 0.92 | 4.11 | 0.87 | 4.08 |
| Nd. 5 | Example 5 | Embodiment 7 | 0.88 | 4.09 | 0.89 | 4.08 | 0.88 | 4.14 |
| NO. 6 | Example 6 | Embodiment 7 | 0.93 | 3.91 | 0.93 | 3.92 | 0.92 | 3.97 |
| NO. 7 | Example 7 | Embodiment 7 | 0.87 | 4.03 | 0.91 | 4.01 | 0.89 | 4.02 |
| NO. 8 | Example 8 | Embodiment 7 | 0.92 | 3.89 | 0.88 | 3.83 | 0.89 | 3.84 |
| NO. 9 | Example 9 | Embodiment 7 | 0.93 | 3.88 | 0.90 | 3.87 | 0.88 | 3.86 |
| NO. 10 | Example 10 | Embodiment 7 | 0.94 | 3.91 | 0.88 | 3.94 | 0.86 | 3.90 |
| NO. 11 | Example 11 | Embodiment 7 | 0.89 | 3.95 | 0.93 | 3.93 | 0.95 | 3.94 |
| NO. 12 | Example 12 | Embodiment 7 | 0.94 | 3.89 | 0.92 | 3.92 | 0.89 | 3.95 |

Electrification conditions: direct pulse current: 1 mA, frequency: 30 kHz, ON/OFF = 3/7; electrification time: 180 minutes, 1 kΩ resistance serially connected

TABLE 10

| Experimental Example | Anode | Cathode | 1 Hour electrification | | 2 Hours electrification | | 3 Hours electrification | |
|---|---|---|---|---|---|---|---|---|
| | | | Transport current | Voltage (V) | Transport Current | Voltage (V) | Transport Current | Voltage (V) |
| NO. 13 | Example 13 | Embodiment 7 | 0.87 | 3.97 | 0.94 | 3.95 | 0.91 | 3.93 |
| NO. 14 | Example 14 | Embodiment 7 | 0.86 | 4.01 | 0.88 | 3.93 | 0.88 | 3.97 |
| NO. 15 | Example 15 | Embodiment 7 | 0.93 | 3.98 | 0.92 | 4.04 | 0.90 | 4.02 |
| NO. 16 | Example 16 | Embodiment 7 | 0.88 | 4.18 | 0.92 | 4.15 | 0.91 | 4.12 |
| NO. 17 | Example 17 | Embodiment 7 | 0.92 | 3.88 | 0.89 | 3.89 | 0.86 | 3.93 |
| NO. 18 | Example 9 | Example 18 | 0.96 | 3.87 | 0.91 | 3.74 | 0.93 | 3.84 |
| NO. 19 | Example 9 | Example 19 | 0.93 | 3.84 | 0.95 | 3.82 | 0.94 | 3.91 |
| NO. 20 | Example 9 | Example 20 | 0.89 | 3.85 | 0.91 | 3.89 | 0.87 | 3.87 |
| NO. 21 | Comparative example 1 | Embodiment 7 | 0.97 | 3.24 | 0.93 | 3.35 | 0.94 | 3.26 |
| NO. 22 | Comparative example 2 | Embodiment 7 | 0.15 | 5.08 | 0.25 | 5.16 | 0.23 | 5.19 |
| NO. 23 | Example 9 | Comparative example 2 | 0.19 | 5.48 | 0.18 | 5.47 | 0.23 | 5.53 |

Electrification conditions: direct pulse current: 1 mA, frequency: 30 kHz, ON/OFF = 3/7, electrification time: 180 minutes, 1 kΩ resistance serially connected

TABLE 11

| Experimental Example | Anode | Cathode | Initial pH value | pH value after 3 hours electrification |
|---|---|---|---|---|
| NO. 24 | Example 21 | Embodiment 7 | 9.83 | 9.71 |
| NO. 25 | Example 22 | Embodiment 7 | 9.60 | 9.50 |
| NO. 26 | Example 23 | Embodiment 7 | 10.13 | 9.85 |
| NO. 27 | Example 24 | Embodiment 7 | 10.06 | 9.73 |
| NO. 28 | Example 25 | Embodiment 7 | 4.38 | 3.85 |
| NO. 29 | Example 26 | Embodiment 7 | 4.03 | 3.63 |
| NO. 30 | Example 27 | Embodiment 7 | 4.15 | 3.79 |
| NO. 31 | Example 28 | Embodiment 7 | 4.27 | 3.88 |
| NO. 32 | Example 29 | Embodiment 7 | 10.53 | 9.71 |
| NO. 33 | Example 30 | Embodiment 7 | 10.13 | 4.14 |
| NO. 34 | Example 31 | Embodiment 7 | 9.87 | 6.64 |
| NO. 35 | Example 32 | Embodiment 7 | 10.88 | 9.85 |
| NO. 36 | Example 33 | Embodiment 7 | 9.78 | 3.54 |
| NO. 37 | Example 34 | Embodiment 7 | 9.89 | 3.68 |
| NO. 38 | Example 35 | Embodiment 7 | 8.15 | 4.18 |
| NO. 39 | Example 36 | Embodiment 7 | 3.34 | 3.69 |
| NO. 40 | Example 37 | Embodiment 7 | 8.95 | 4.32 |
| NO. 41 | Example 38 | Embodiment 7 | 9.31 | 3.78 |
| NO. 42 | Example 39 | Embodiment 7 | 7.15 | 6.87 |
| NO. 43 | Example 40 | Embodiment 7 | 6.83 | 6.53 |
| NO. 44 | Example 41 | Embodiment 7 | 8.31 | 4.15 |
| NO. 45 | Comparative example 3 | Embodiment 7 | 2.57 | 1.01 |
| NO. 46 | Comparative example 4 | Embodiment 7 | 10.76 | 1.58 |

Electrification conditions: pulse current: 1 mA, frequency: 30 kHz, ON/OFF = 3/7, electrification time: 3 hours

TABLE 12

| Experimental Example | Anode | Cathode | Initial pH value | pH value after 3 hours electrification |
|---|---|---|---|---|
| NO. 47 | Embodiment 9 | Example 42 | 6.30 | 10.58 |
| NO. 48 | Embodiment 9 | Example 43 | 6.12 | 9.88 |
| NO. 49 | Embodiment 9 | Example 44 | 5.88 | 9.42 |
| NO. 50 | Embodiment 9 | Example 45 | 4.80 | 9.84 |
| NO. 51 | Embodiment 9 | Example 46 | 6.51 | 10.51 |
| NO. 52 | Embodiment 9 | Example 47 | 6.48 | 10.14 |

TABLE 12-continued

| Experimental Example | Anode | Cathode | Initial pH value | pH value after 3 hours electrification |
|---|---|---|---|---|
| NO. 53 | Embodiment 9 | Example 48 | 6.40 | 9.99 |
| NO. 54 | Embodiment 9 | Example 49 | 8.83 | 11.82 |
| NO. 55 | Embodiment 9 | Example 50 | 6.87 | 8.88 |
| NO. 56 | Embodiment 9 | Example 51 | 8.94 | 11.81 |
| NO. 57 | Embodiment 9 | Example 52 | 10.74 | 11.95 |
| NO. 58 | Embodiment 9 | Example 53 | 6.58 | 11.42 |
| NO. 59 | Embodiment 9 | Example 54 | 6.41 | 11.37 |
| NO. 60 | Embodiment 9 | Example 55 | 7.01 | 11.97 |
| NO. 61 | Embodiment 9 | Example 56 | 6.63 | 11.77 |
| NO. 62 | Embodiment 9 | Example 57 | 6.89 | 11.93 |
| NO. 63 | Embodiment 9 | Example 58 | 6.57 | 11.65 |
| NO. 64 | Embodiment 9 | Example 59 | 8.50 | 11.96 |
| NO. 65 | Embodiment 9 | Example 60 | 7.94 | 11.87 |
| NO. 66 | Embodiment 9 | Example 61 | 7.81 | 11.57 |
| NO. 67 | Embodiment 9 | Comparative Example 5 | 6.53 | 13.12 |
| NO. 68 | Embodiment 9 | Comparative Example 6 | 7.00 | 12.57 |

Electrification conditions: pulse current: 1 mA, frequency: 30 kHz, ON/OFF = 3/7, electrification time: 3 hours

TABLE 13

| Experimental Example | Anode | Cathode | Local anesthetic effect index after each electrification (%) | | | | |
|---|---|---|---|---|---|---|---|
| | | | 15 min | 30 min | 60 min | 90 min | 120 min |
| NO. 69 | Example 62 | Embodiment 70 | 80 | 160 | — | — | — |
| NO. 70 | Example 63 | Embodiment 70 | 70 | 140 | — | — | — |
| NO. 71 | Example 64 | Embodiment 70 | 70 | 140 | — | — | — |
| NO. 72 | Example 65 | Embodiment 70 | 70 | 120 | — | — | — |
| NO. 73 | Example 66 | Embodiment 70 | 80 | 140 | — | — | — |
| NO. 74 | Example 67 | Embodiment 70 | 70 | 120 | — | — | — |
| NO. 75 | Comparative example 7 | Embodiment 70 | 0 | 22 | 32 | 44 | 60 |

Electrification conditions: pulse current: 6 mA, frequency: 30 kHz, ON/OFF = 3/7, electrification time: No. 69–No. 74: 30 minutes, No. 75: 120 minutes

TABLE 14

| Judgment | Criteria | Score |
|---|---|---|
| − | Painful (no difference from untreated areas) | 0.0 |
| (±) | Slightly painful | 0.2 |
| ± | Sensitive to touch but not painful | 0.5 |
| + | Not painful (difficult to discern touch) | 1.0 |
| ++ | No feeling | 2.0 |

Effect index: (total score/number of test cases) × 100 effective value > 100

TABLE 15

| Experimental Example | Anode | Cathode | $C_{max}$(ng/ml) | $AUC_{0-2h}$(ng · ml$^{-1}$ · h) | Irritation or coloration |
|---|---|---|---|---|---|
| NO. 76 | Example 68 | Example 70 | 1.19 | 14.90 | None (anode or cathode) |
| NO. 77 | Comparative example 8 | Comparative example 14 | 0.03 | 0.30 | None (anode or cathode) |
| NO. 78 | Comparative example 9 | Comparative example 14 | 0.24 | 2.95 | Redness (anode) |
| NO. 79 | Comparative example 10 | Comparative example 14 | 0.61 | 7.24 | Blackening (anode) |
| NO. 80 | Comparative example 11 | Comparative example 14 | 0.17 | 2.21 | None (anode or cathode) |

Electrification conditions: pulse current: 2 mA, frequency: 30 kHz, ON/OFF = 3/7, electrification time: 60 minutes

TABLE 16

| Experimental Example | Anode | Cathode | $C_{max}$(ng/ml) | $AUC_{0-2h}$(ng · ml$^{-1}$ · h) | Irritation or coloration |
|---|---|---|---|---|---|
| NO. 81 | Example 71 | Example 69 | 19.20 | 241.65 | None (anode or cathode) |
| NO. 82 | Comparative example 14 | Comparative example 12 | 1.60 | 21.45 | Redness (anode) |

Electrification conditions: pulse current: 2 mA, frequency: 30 kHz, ON/OFF = 3/7, electrification time: 60 minutes

What is claimed is:

1. An iontophoresis electrode device comprising an inert electrode member, an electrolyte solvent, a depolarizer preventing polarization of said inert electrode member and a pH regulator which is poorly soluble in said electrolyte solvent for use in said device.

2. An iontophoresis electrode device according to claim 1, characterized by including a buffering agent dispersed or dissolved in a gel packed in said device, or mixed with said electrolyte solvent.

3. An iontophoresis electrode device according to claim 2 characterized by being further provided with a backing having an edge section defining an opening, said backing being formed in a cup shape with a packing chamber inside the cup shape, an electrode terminal situated at a hole formed from said backing in a ceiling of said packing chamber, said inert electrode member covering a base of said electrode terminal in said packing chamber, an adhesive layer formed on said edge section, and a liner which is attached to said adhesive layer and covers said opening.

4. An iontophoresis electrode device according to claim 3, characterized by being provided with a non-adhesive gel containing an electrolyte solvent packed in said packing chamber.

5. An iontophoresis electrode device according to claim 4, characterized in that said non-adhesive gel contains at least one of said depolarizer, said pH regulator and a drug.

6. An iontophoresis electrode device according to claim 5, characterized by being provided with said drug contained in said non-adhesive gel and a holding material which holds said depolarizer and/or said pH regulator.

7. An iontophoresis electrode device according to claim 3, characterized by being provided with a powder mixture included in said packing chamber, a cover member covering said opening, an adhesive layer formed on said cover member across said cover member and said edge section, an injection hole open from said backing surface to the ceiling side of said packing chamber, and a stopper for sealing said injection hole.

8. An iontophoresis electrode device according to claim 1 characterized by being further provided with a backing having an edge section defining an opening, said backing being formed in a cup shape with a packing chamber inside the cup shape, an electrode terminal situated at a hole formed from said backing in a ceiling of said packing chamber, said inert electrode member covering a base of said electrode terminal in said packing chamber, an adhesive layer formed on said edge section, and a liner which is attached to said adhesive layer and covers said opening.

9. An iontophoresis electrode device according to claim 8, characterized by being provided with a non-adhesive gel containing an electrolyte solvent packed in said packing chamber.

10. An iontophoresis electrode device according to claim 9, characterized in that said non-adhesive gel contains at least one of said depolarizer, said pH regulator and a drug.

11. An iontophoresis electrode device according to claim 10, characterized by being provided with said drug contained in said non-adhesive gel and a holding material which holds said depolarizer and/or said pH regulator.

12. An iontophoresis electrode device according to claim 8, characterized by being provided with a powder mixture included in said packing chamber, a cover member covering said opening, an adhesive layer formed on said cover member across said cover member and said edge section, an injection hole open from said backing surface to the ceiling side of said packing chamber, and a stopper for sealing said injection hole.

13. An iontophoresis electrode device according to claim 12, characterized in that the powder mixture included in said packing chamber contains at least one of said depolarizer, said pH regulator and a drug.

14. An iontophoresis electrode device according to claim 12, characterized in that an electrolyte solution injected through said injection hole contains at least one of the depolarizer and drug in said electrolyte solvent.

15. An iontophoresis electrode device according to claim 12, characterized in that the powder mixture included in the packing chamber contains at least one of said depolarizer, a pH regulator and a drug, and said electrolyte solution is prepared by dissolving in said electrolyte solvent at least one of a depolarizer and a drug other than said depolarizer or said drug in said powder mixture.

16. An ioncophoresis electrode device according to claim 7, characterized in that the powder mixture included in said packing chamber contains at least one of said depolarizer, said pH regulator and a drug.

17. An iontophoresis electrode device according to claim 7, characterized in that an electrolyte solution injected through said injection hole contains at least one of the depolarizer and drug in said electrolyte solvent.

18. An iontophoresis electrode device according to claim 7, characterized in that the powder mixture included in the packing chamber contains at least one of said depolarizer, a pH regulator and a drug, and an electrolyte solution is prepared by dissolving in said electrolyte solvent at least one of a depolarizer and a drug other than said depolarizer or said drug in said powder mixture.

19. An iontophoresis electrode device according to any one of claims 1, 10, 13, 14, 15 and 16 through 18 characterized in that said depolarizer is an electrode reactive substance which has electrode reactivity such that it is preferentially oxidized over hydroxide ions and chloride ions at said inert electrode member, and whose reaction product readily dissolves in said electrolyte solvent.

20. An iontophoresis electrode device according to claim 19, characterized in that said depolarizer is at least one depolarizer selected from the group consisting of ascorbic acid, erythorbic acid, cysteine, acetylcysteine, thioglycolic acid, thiomalic acid or their salts, sulfites, bisulfites, thiosulfates, pyrosulfites, nitrites, iodides and α-thioglycerine.

21. An iontophoresis electrode device according to any one of claims 1, 10, 13, 14, 15 and 16 through 18 characterized in that said depolarizer is an electrode reactive substance which has electrode reactivity such that it is preferentially reduced over hydrogen ions at said inert electrode member, and whose reaction product readily dissolves or has high conductivity in said electrolyte solvent.

22. An iontophoresis electrode device according to claim 21, characterized in that said depolarizer is at least one selected from the group consisting of iron (III) compounds, copper (II) compounds and hydrogen peroxide.

23. An iontophoresis electrode device according to claim 22, wherein said iron III compound is ferric chloride and said copper II compound is copper sulfate.

24. An iontophoresis electrode device according to any one of claims 1, 10, 11, 13, 14, 15 and 16 through 18 characterized in that said pH regulator is a basic oxide or basic hydroxide or a mixture thereof.

25. An iontophoresis electrode device according to claim 24, wherein the basic oxide is at least one selected from the group consisting of calcium oxide and magnesium oxide and/or the basic hydroxide is at least one hydroxide selected from the group consisting of calcium hydroxide, magnesium hydroxide and hydroxyapatite.

26. An iontophoresis electrode device according to any one of claims 1, 10, 11, 13, 14, 15 and 16 through 18 characterized in that said pH regulator is a silicic acid or acid anhydride or a mixture thereof.

27. An iontophoresis electrode device according to claim 25, wherein the silicic acid or acid anhydride is selected from the group consisting of silica gel, light silicic anhydride, phthylic anhydride and isobutylene-maleic anhydride copolymer.

28. An iontophoresis electrode device according to any one of claims 1, 10, 11, 13, 14, 15 and 16 through 18 characterized in that said pH regulator is an amphoteric oxide, amphoteric hydroxide, aluminate, aluminosilicate or silicate or compound salt thereof, or a mixture thereof.

29. An ioniophoresis electrode device according to claim 28, wherein the amphoteric oxide, amphoteric hydroxide, aluminate, aluminosilicate or silicate or compound salt thereof is selected from the group consisting of γ-alumina, aluminum hydroxide, dry aluminum hydroxide gel, magnesium aluminum hydroxide, aluminum glycinate, synthetic hydrotalcite, zeolite, synthetic aluminum silicate, natural aluminum silicate, magnesium aluminosilicate, magnesium aluminometasilicate, bismuth magnesium aluminosilicate, magaldrate, calcium silicate, magnesium silicate and zinc oxide.

30. An iontophoresis electrode device according to any one of claims 10, 13, 14, 15 and 16 through 18 characterized in that said drug is a cationic drug.

31. An iontophoresis electrode device according to any one of claims 10, 11, 14, 15 and 16 through 18 characterized in that said drug is an anionic drug.

* * * * *